US008356644B2

(12) United States Patent
Chong et al.

(10) Patent No.: US 8,356,644 B2
(45) Date of Patent: Jan. 22, 2013

(54) TRANSFER GUARD SYSTEMS AND METHODS

(75) Inventors: Colin A. Chong, Burbank, CA (US); Julian D. Kavazov, Arcadia, CA (US); Rafael Bikovsky, Oak Park, CA (US); Arsen Ibranyan, Glendale, CA (US); Eric M. Lorenzen, Granada Hills, CA (US); Chad Srisathapat, Sun Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 771 days.

(21) Appl. No.: 12/537,579

(22) Filed: Aug. 7, 2009

(65) Prior Publication Data

US 2011/0030845 A1 Feb. 10, 2011

(51) Int. Cl.
*B65B 1/04* (2006.01)
(52) U.S. Cl. ......... 141/329; 141/319; 141/330; 604/412
(58) Field of Classification Search .................. 141/319, 141/329, 330; 604/412
See application file for complete search history.

(56) References Cited

U.S. PATENT DOCUMENTS

| | | | | |
|---|---|---|---|---|
| 3,807,464 A | * | 4/1974 | Pitesky | 141/97 |
| 3,833,030 A | * | 9/1974 | Waldbauer et al. | 141/26 |
| 3,844,318 A | * | 10/1974 | Raia et al. | 141/27 |
| D247,576 S | * | 3/1978 | Ekberg | D24/130 |
| 4,092,546 A | * | 5/1978 | Larrabee | 250/515.1 |
| 4,219,055 A | * | 8/1980 | Wright | 141/27 |
| 4,274,453 A | * | 6/1981 | Lee | 141/1 |
| 4,357,971 A | * | 11/1982 | Friedman | 604/218 |
| 4,434,820 A | * | 3/1984 | Glass | 141/2 |
| 4,697,622 A | * | 10/1987 | Swift et al. | 141/1 |
| 4,998,570 A | * | 3/1991 | Strong | 141/27 |
| 5,358,501 A | * | 10/1994 | Meyer | 604/414 |
| 5,385,559 A | * | 1/1995 | Mannix | 604/211 |
| 5,468,233 A | * | 11/1995 | Schraga | 604/207 |

(Continued)

FOREIGN PATENT DOCUMENTS

| | | |
|---|---|---|
| EP | 1 145 702 A2 | 10/2001 |
| FR | 2636537 | 3/1990 |

(Continued)

OTHER PUBLICATIONS

International Search Report and Written Opinion dated Nov. 30, 2010; Mailed Dec. 6, 2012, from related patent application No. PCT/US2010/044159.

(Continued)

*Primary Examiner* — Timothy L Maust
(74) *Attorney, Agent, or Firm* — Foley & Lardner LLP

(57) ABSTRACT

A transfer guard may provide a fluid path from a vial to a reservoir containing a plunger head connected to a plunger arm operatively engagable with a handle that at least partially covers a casing configured to allow the handle to operatively engage the plunger arm to move the plunger head to transfer fluidic media from the vial to the reservoir.

A support structure may have a chamber, a first adapter for mating with a vial containing fluidic media, and a second adapter for mating with a reservoir containing a plunger head moveable within the reservoir. A first needle may provide a fluid path from the vial to the reservoir and a second needle may connect the vial and the chamber containing an air flow control mechanism for allowing air to flow in one direction.

15 Claims, 19 Drawing Sheets

U.S. PATENT DOCUMENTS

| | | | |
|---|---|---|---|
| D370,974 S * | 6/1996 | Barresi et al. | D24/111 |
| 5,653,686 A * | 8/1997 | Coulter et al. | 222/1 |
| 5,697,916 A * | 12/1997 | Schraga | 604/207 |
| 5,902,280 A * | 5/1999 | Powles et al. | 604/240 |
| 6,439,276 B1 * | 8/2002 | Wood et al. | 141/97 |
| 7,086,431 B2 * | 8/2006 | D'Antonio et al. | 141/330 |
| 7,882,860 B2 * | 2/2011 | Spitz | 141/27 |
| 7,963,954 B2 * | 6/2011 | Kavazov | 604/403 |
| 8,141,601 B2 * | 3/2012 | Fehr et al. | 141/346 |
| 2007/0106244 A1 | 5/2007 | Mosler et al. | |
| 2009/0124982 A1 | 5/2009 | Jimenez | |

FOREIGN PATENT DOCUMENTS

| | | |
|---|---|---|
| WO | WO 84/04672 | 12/1984 |
| WO | WO-00/57835 | 10/2000 |
| WO | WO-2009/065932 A | 5/2009 |

OTHER PUBLICATIONS

Partial International Search Report dated Nov. 30, 2010 from related patent application No. PCT/US2010/044159.

* cited by examiner

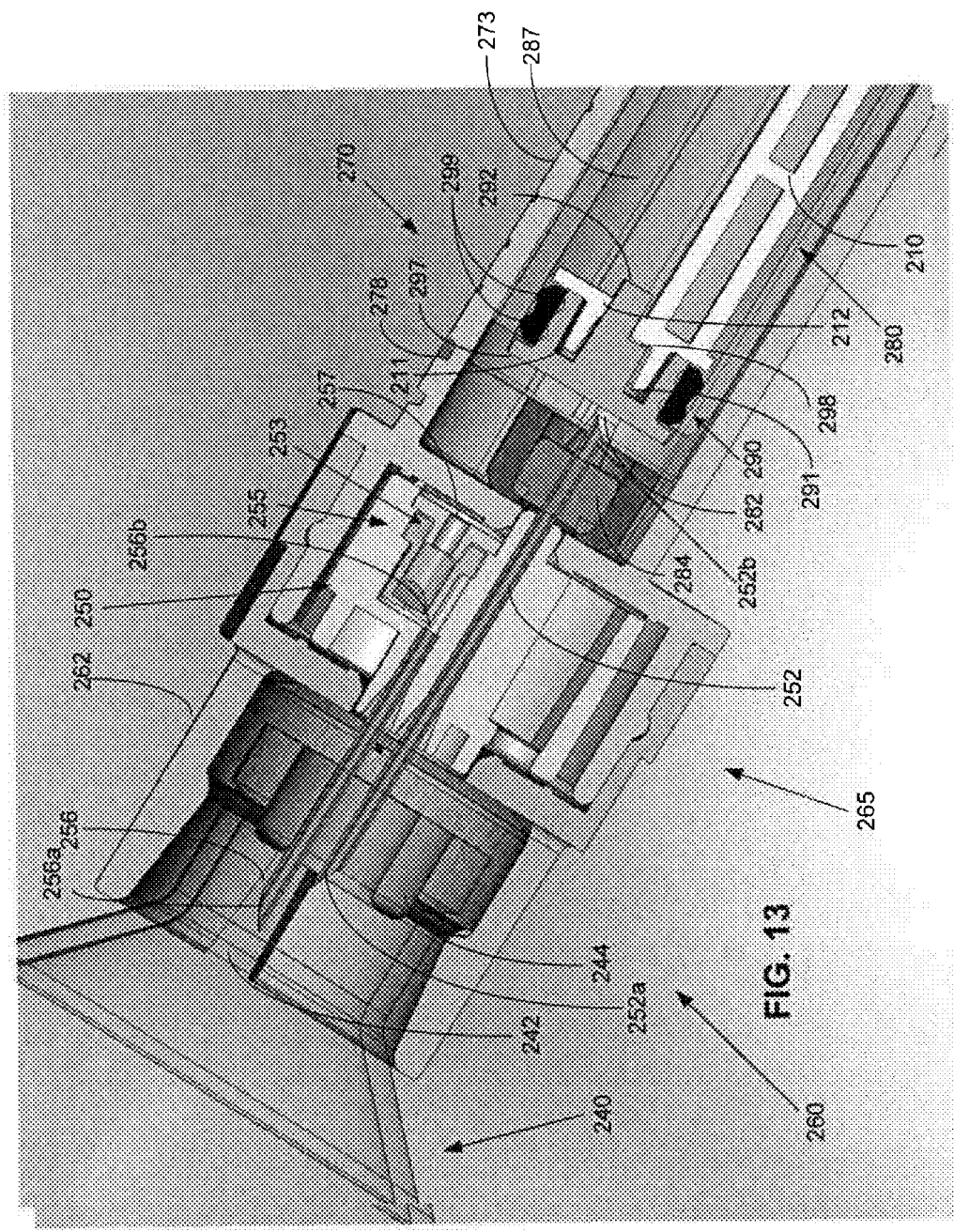

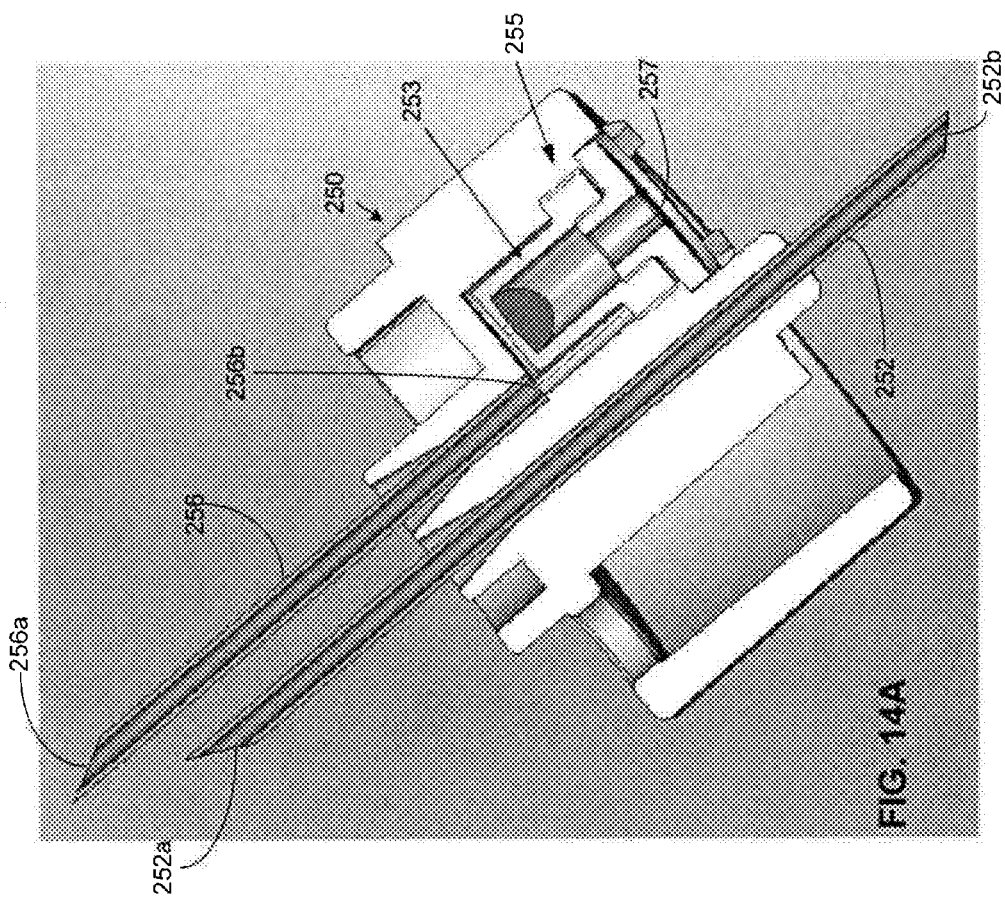

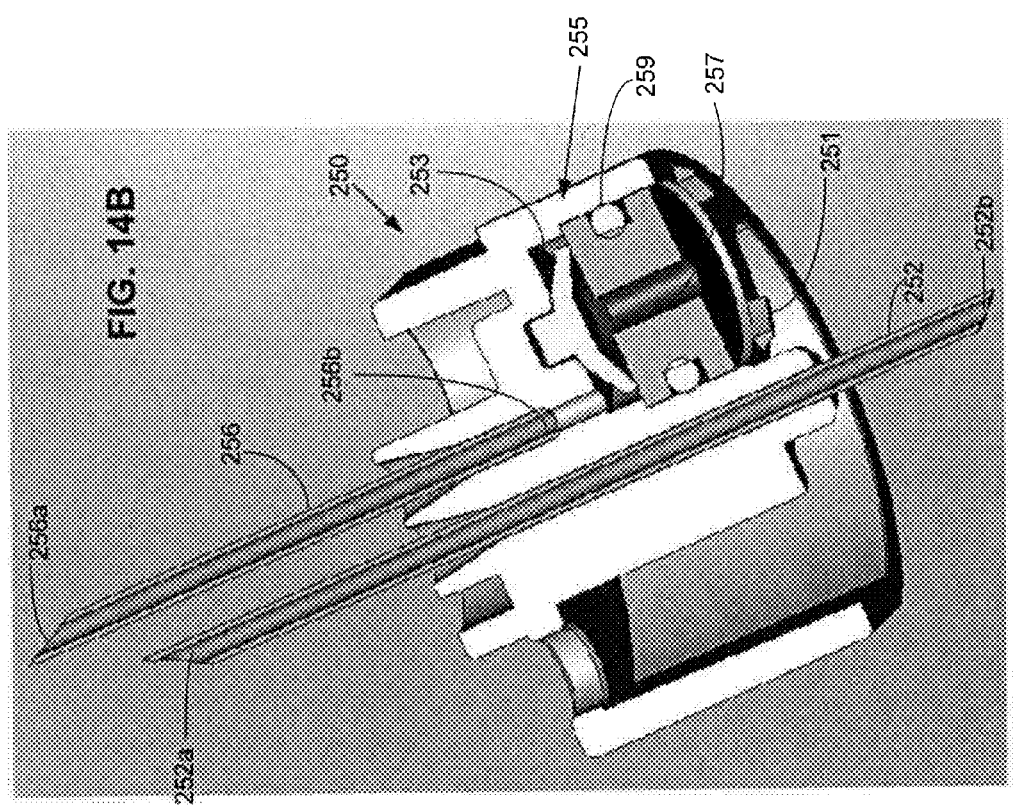

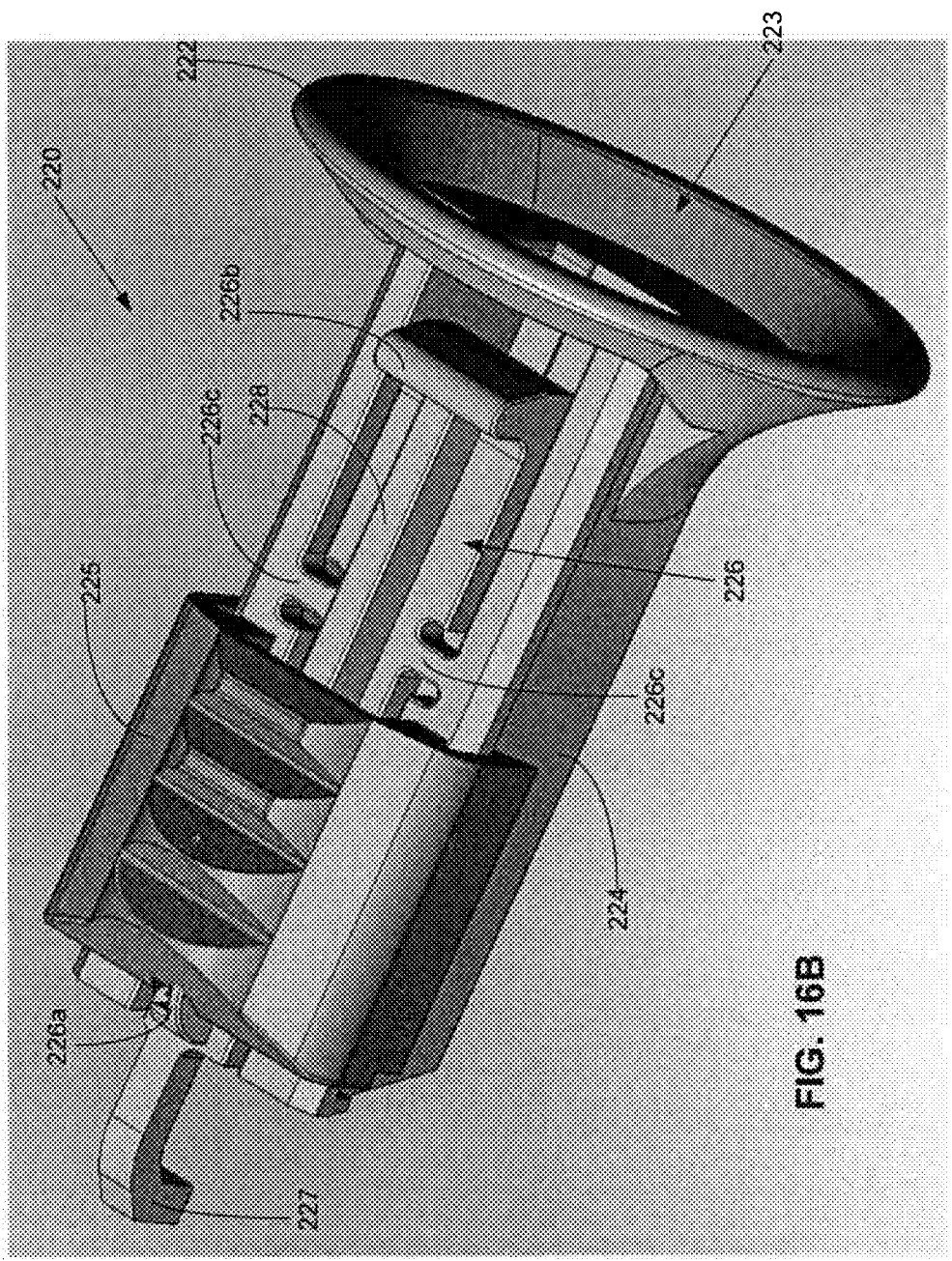

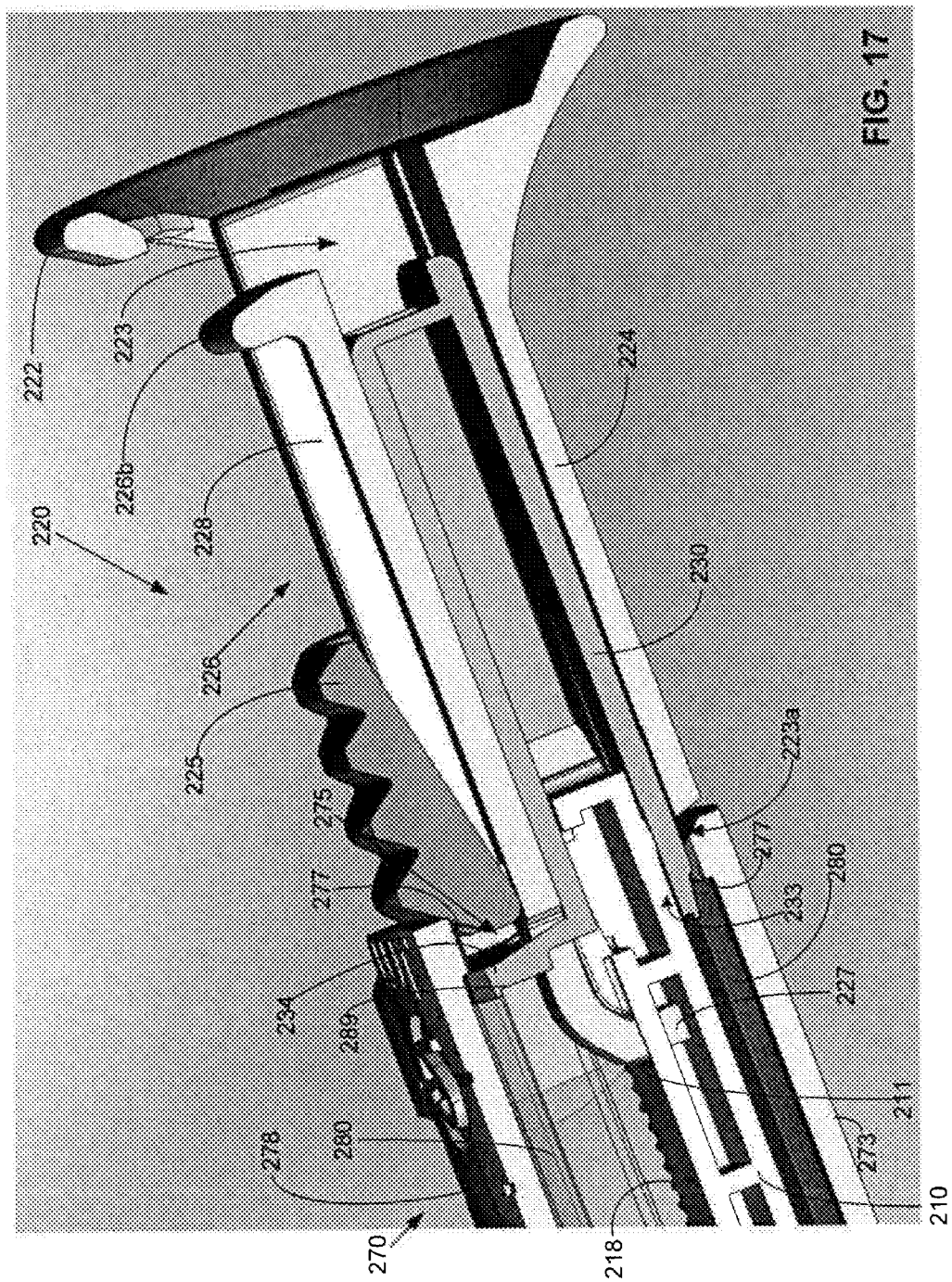

TRANSFER GUARD SYSTEMS AND METHODS

BACKGROUND

1. Field of the Invention

Embodiments of the present invention generally relate to systems and methods with reservoirs, and, in specific embodiments, to systems and methods for assisted filling of reservoirs.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A system for transferring fluidic media may include, but is not limited to, a transfer guard, a handle, and a casing. The transfer guard may be for providing a fluid path from a vial to a reservoir. The handle may be configured to be operatively engagable to a plunger arm connected to a plunger head arranged for movement in an axial direction of the reservoir. The casing may be configured to allow the plunger arm to move in the axial direction relative to the reservoir to move the plunger head in the axial direction within the reservoir. The handle may be configured to cover at least a portion of the casing The transfer guard and the handle may be configured such that fluidic media is transferred from the vial to the reservoir in a case where the handle is operatively engaged to the plunger arm and the handle is moved relative to the axial direction relative to the reservoir.

In various embodiments, the casing may have an opening for allowing the handle to operatively engage the plunger arm. In various embodiments, the handle may include an engagement portion configured for pivotal movement to operatively engage and disengage the plunger arm. In some embodiments, the handle may include a slide adapted to cause the pivotal movement of the engagement portion to operatively engage and disengage the plunger arm. In further embodiments, the slide may be adapted to move at least between a first position and a second position. The engagement portion may be configured to engage the plunger arm when the slide is moved to the first position. The engagement portion may be configured to disengage the plunger arm when the slide is moved to the second position.

In some embodiments, the engagement portion may have an extension. The plunger arm may have an aperture for receiving the extension when the engagement portion of the handle operatively engages the plunger arm. In further embodiments, the extension of the engagement portion may be for extending through an opening in the casing to operatively engage the aperture in the plunger arm and for allowing the extension of the engagement portion to move along the opening as the plunger arm is moved by the handle.

In various embodiments, the transfer guard may have an end for mating with the reservoir. The end may comprise a body configured to envelop the reservoir. In some embodiments, the body may be adapted to allow fluidic media in the reservoir to be viewable through the body in a case where the reservoir is connected to the end of the transfer guard and the reservoir contains fluidic media. In further embodiments, the body may have an opening for allowing fluidic media in the reservoir to be viewable and for allowing a user-patient to provide further support to the reservoir during use of the system. In some embodiments, the body may have one or more fill lines for measuring a volume of fluidic media in the reservoir.

In various embodiments, the transfer guard may have a chamber. The transfer guard may include, but is not limited to, a first needle, a second needle, and an air flow control mechanism. The first needle may be for connecting the interior volume of the vial to the interior volume of the reservoir to provide a fluid flow path from the interior volume of the vial to the interior volume of the reservoir. The second needle may be for connecting the chamber and the interior volume of the vial. The air flow control mechanism may be arranged within the chamber and configured to allow air to flow in one direction in a case where the second needle connects the chamber and the vial and the plunger head is moved within the reservoir to transfer fluidic media from the interior volume of the vial to the interior volume of the reservoir.

In some embodiments, the air flow control mechanism may be configured to allow the chamber to communicate with atmosphere to equalize pressure relative to atmosphere in the interior volume of the vial in a case where the second needle connects the chamber and the vial and the plunger head is moved within the reservoir to transfer fluidic media from the interior volume of the vial to the interior volume of the reservoir. In some embodiments, the air flow control mechanism may comprise a membrane configured to allow air to flow in one direction. In some embodiments, the air flow control mechanism may comprise a valve. In further embodiments, the valve may comprise at least one of an umbrella valve and a duckbill valve configured to allow air to flow in one direction.

A method of making a system for transferring fluidic media may include, but is not limited to, any one of or combination of: (i) providing a transfer guard for providing a fluid path from a vial to a reservoir; (ii) configuring a handle to be operatively engagable to a plunger arm connected to a plunger head arranged for movement in an axial direction of the reservoir; (iii) configuring a casing to allow the plunger arm to move in the axial direction relative to the reservoir to move the plunger head in the axial direction within the reservoir; (iv) configuring the handle to cover at least a portion of the casing; and (v) configuring the transfer guard and the handle such that fluidic media is transferred from the vial to the reservoir in a case where the handle is operatively engaged to the plunger arm and the handle is moved in the axial direction relative to the reservoir.

A system for transferring fluidic media may include, but is not limited to, a support structure, a first needle, a second needle, and an air flow control mechanism. The support structure may have a chamber. The support structure may include, but is not limited to a first adapter and a second adapter. The first adapter may be adapted to be mated to a vial having an interior volume containing fluidic media. The second adapter may be adapted to be mated to a reservoir having an interior volume for containing fluidic media and a plunger head arranged for movement within the reservoir.

The first needle may be for connecting the interior volume of the vial to the interior volume of the reservoir to provide a fluid flow path from the interior volume of the vial to the interior volume of the reservoir. The second needle may be for connecting the chamber and the interior volume of the vial. The air flow control mechanism may be arranged within the chamber and configured to allow air to flow in one direction in a case where the second needle connects the chamber and the vial and the plunger head is moved within the reservoir to transfer fluidic media from the interior volume of the vial to the interior volume of the reservoir.

In various embodiments, at least a portion of the first needle may be concentrically arranged within at least a portion of the second needle. In some embodiments, the first needle and the second needle may share a common axis. In some embodiments, an axis of the first needle and an axis of the second needle may be parallel to each other. The axis of the first needle may be offset from the axis of the second needle.

In various embodiments, the air flow control mechanism may be adapted to allow the chamber to communicate with atmosphere to equalize pressure relative to atmosphere in the interior volume of the vial in a case where the second needle connects the chamber and the vial and the plunger head is moved within the reservoir to transfer fluidic media from the interior volume of the vial to the interior volume of the reservoir. In various embodiments, the air flow control mechanism may comprise a membrane. In various embodiments, the air flow control mechanism may comprise a valve. In some embodiments, the air flow control mechanism may comprise at least one of an umbrella valve and a duckbill valve. In some embodiments, the valve may be moveable at least between a first position and a second position. The chamber may be for communicating with atmosphere in a case where the valve is in the second position and the fluid flow path is established.

In various embodiments, the second adapter may comprise a body configured to envelop the reservoir. In some embodiments, the body may be adapted to allow fluidic media in the reservoir to be viewable through the body in a case where the reservoir is connected to the second adapter and the reservoir contains fluidic media. In further embodiments, the body may have an opening for allowing fluidic media in the reservoir to be viewable and for allowing a user-patient to provide further support to the reservoir during use of the system. In some embodiments, the body may have one or more fill lines for measuring a volume of fluidic media in the reservoir.

A method of making a system for transferring fluidic media may include but is not limited to, any one of or combination of: (i) supporting a support structure having a chamber, the support structure comprising: a first adapter adapted to be mated to a vial having an interior volume containing fluidic media; and a second adapter adapted to be mated to a reservoir having an interior volume for containing fluidic media and a plunger head arranged for movement within the reservoir; (ii) connecting the interior volume of the vial to the interior volume of the reservoir to provide a fluid flow path from the interior volume of the vial to the interior volume of the reservoir with a first needle; (iii) connecting the chamber and the interior volume of the vial with a second needle; and (iv) arranging an air flow control mechanism within the chamber and configuring the air flow control mechanism to allow air to flow in one direction in a case where the second needle connects the chamber and the vial and the plunger head is moved within the reservoir to transfer fluidic media from the interior volume of the vial to the interior volume of the reservoir.

BRIEF DESCRIPTION OF THE DRAWINGS

FIG. 13 is a cross-section of a portion of a medical device in accordance with an embodiment of the present invention;

FIG. 14A is a cross-section of a portion of a medical device in accordance with an embodiment of the present invention;

FIG. 14B is a cross-section of a portion of a medical device in accordance with an embodiment of the present invention;

FIG. 16B illustrates a portion of a medical device in accordance with an embodiment of the present invention; and FIG. 17 is a cross-section of a portion of a medical device in accordance with an embodiment of the present invention.

DETAILED DESCRIPTION

Figure 1:
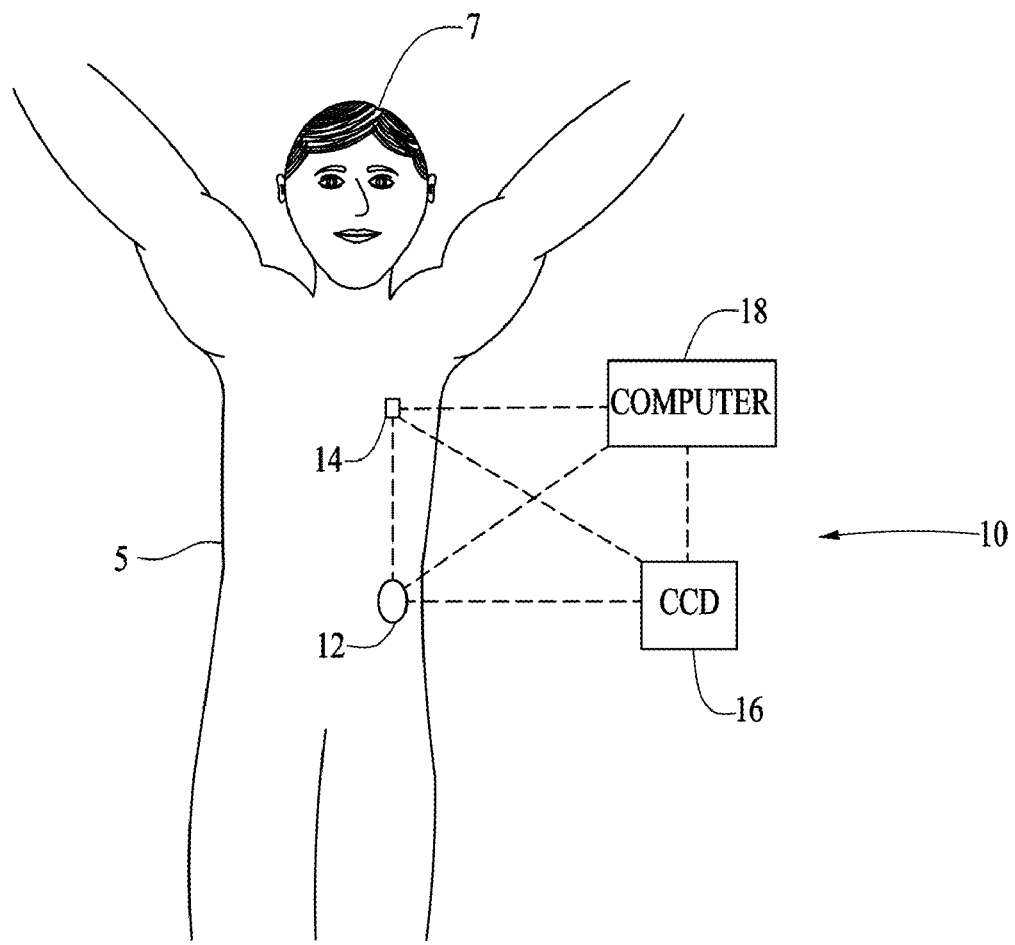
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
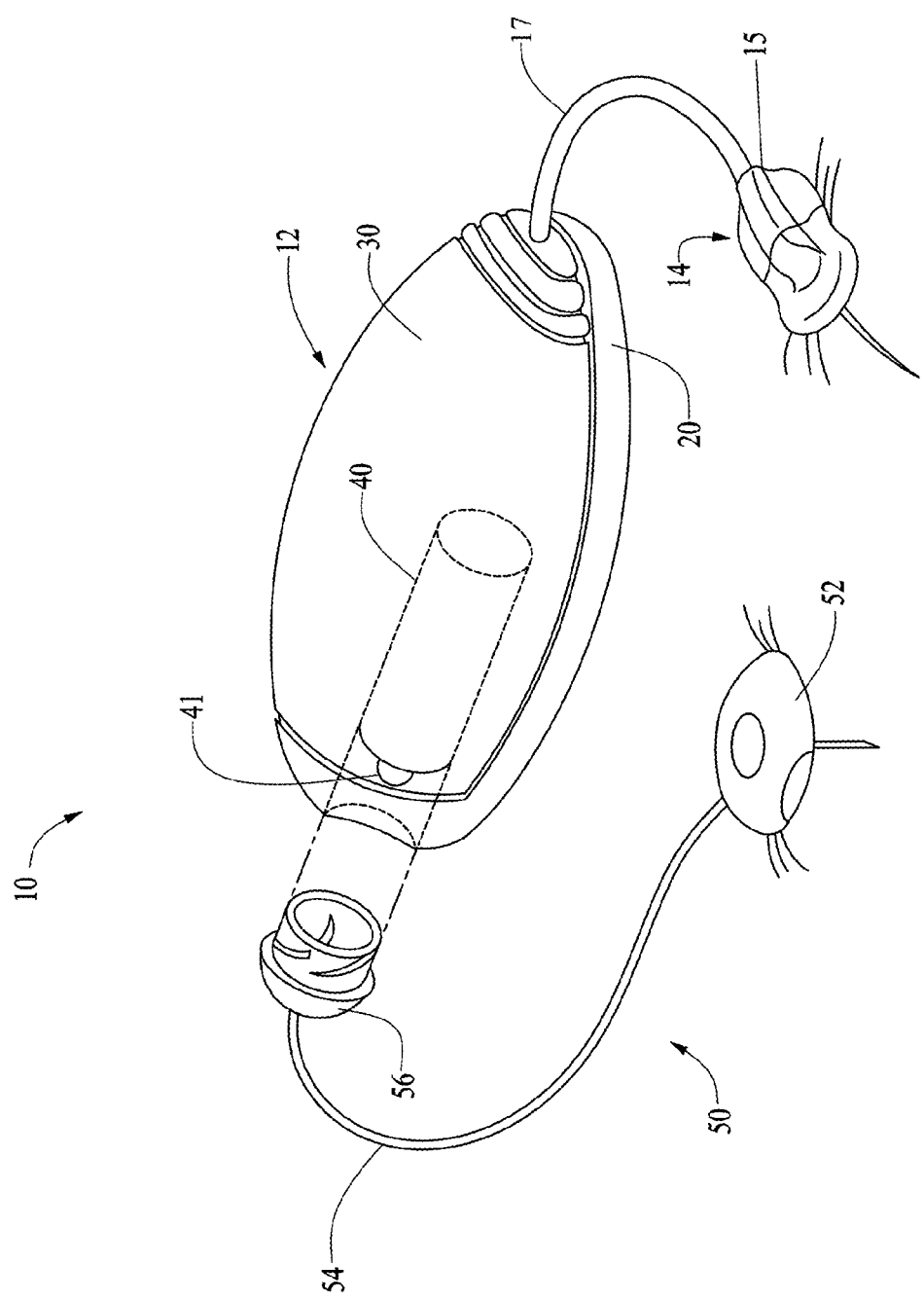
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 includes a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. In addition, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
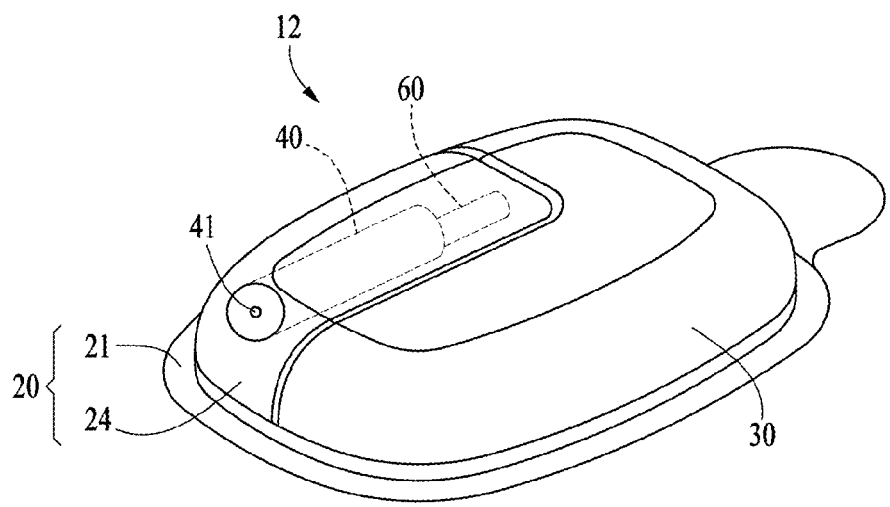
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir retaining portion 24 of the disposable housing 20 is configured to house the reservoir system 40. The reservoir retaining portion 24 of the disposable housing 20 may be configured to have an opening to allow for the port 41 of the reservoir system 40 to be accessed from outside of the reservoir retaining portion 24 while the reservoir system 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
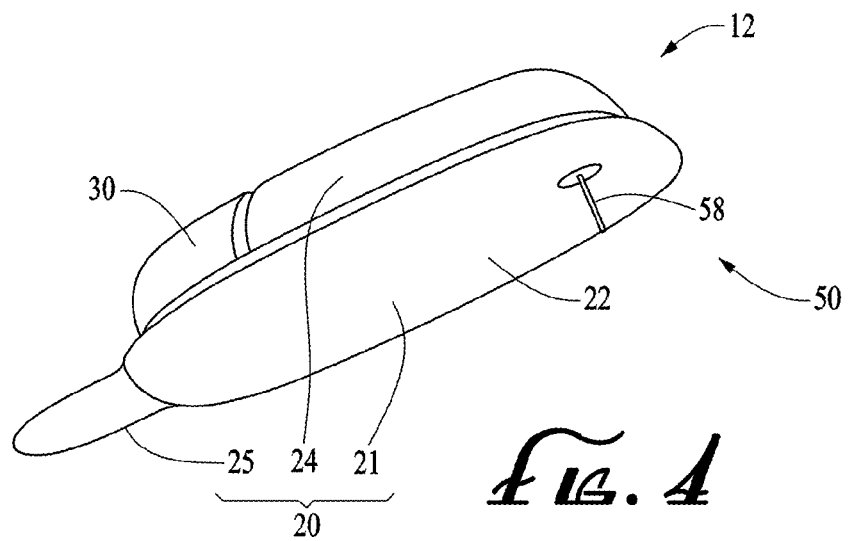
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
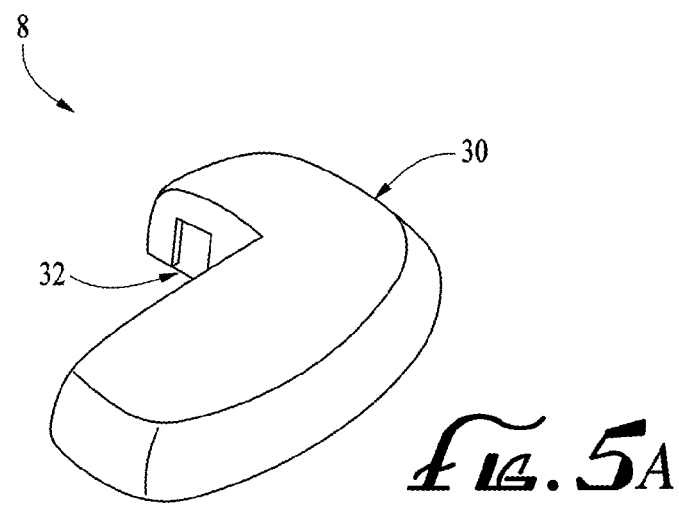
FIG. 5A illustrates a durable portion of a delivery device in accordance with an embodiment of the present invention.
Figure 5B:
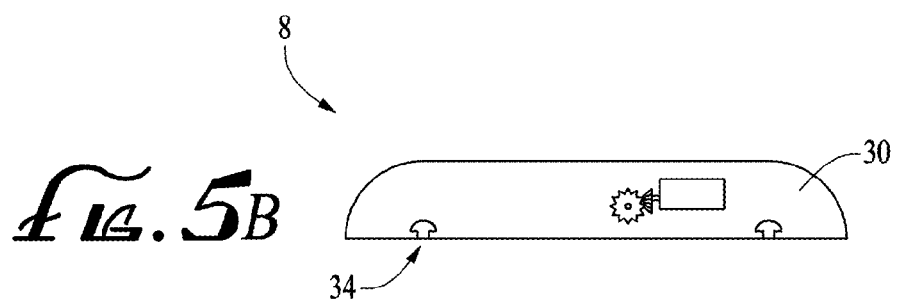
FIG. 5B illustrates a section view of a durable portion of a delivery device in accordance with an embodiment of the present invention.
Figure 5C:
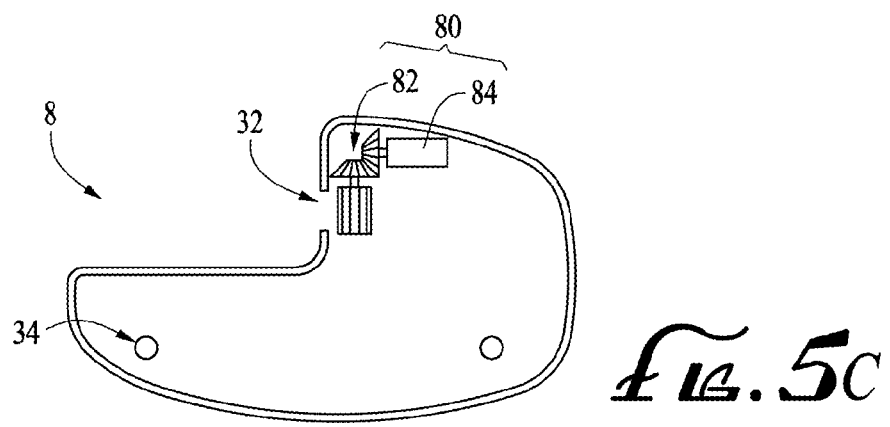
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 is configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
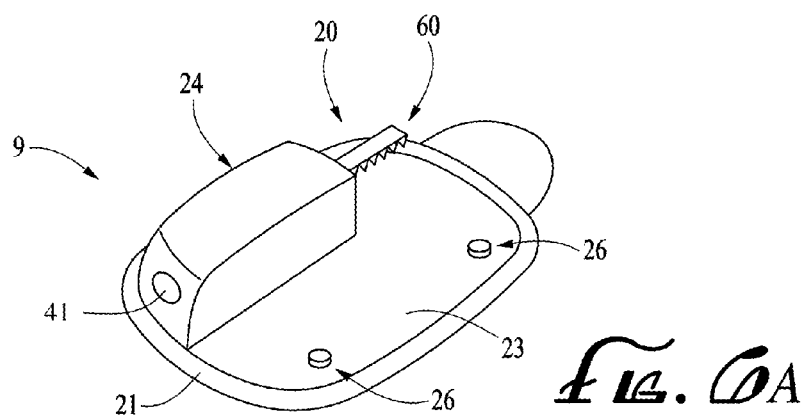
FIG. 6A illustrates a disposable portion of a delivery device in accordance with an embodiment of the present invention.
Figure 6B:
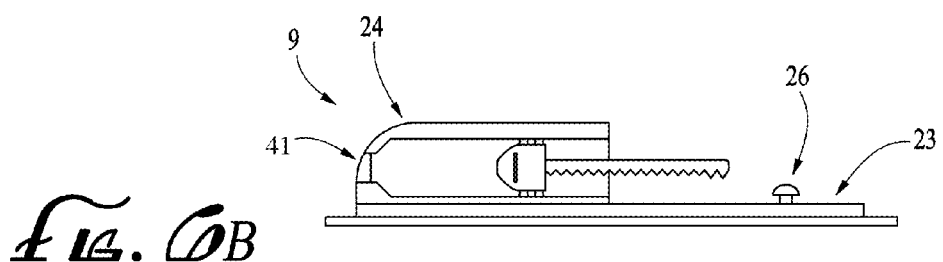
FIG. 6B illustrates a section view of a disposable portion of a delivery device in accordance with an embodiment of the present invention.
Figure 6C:
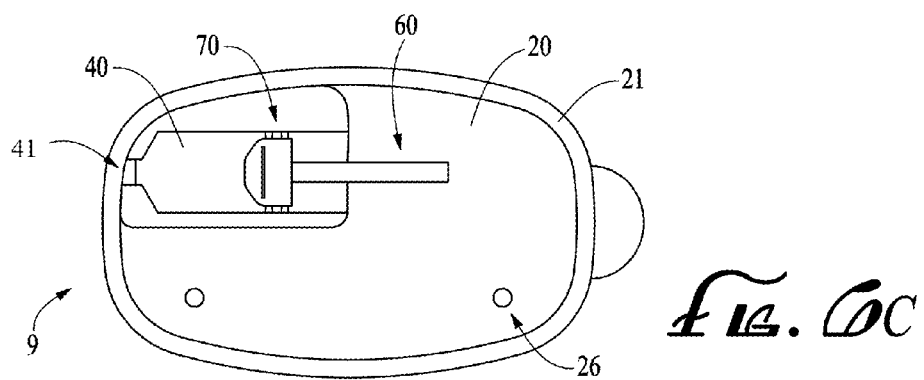
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. In addition, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, to update information in the reservoir circuitry related to an amount of contents remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7:
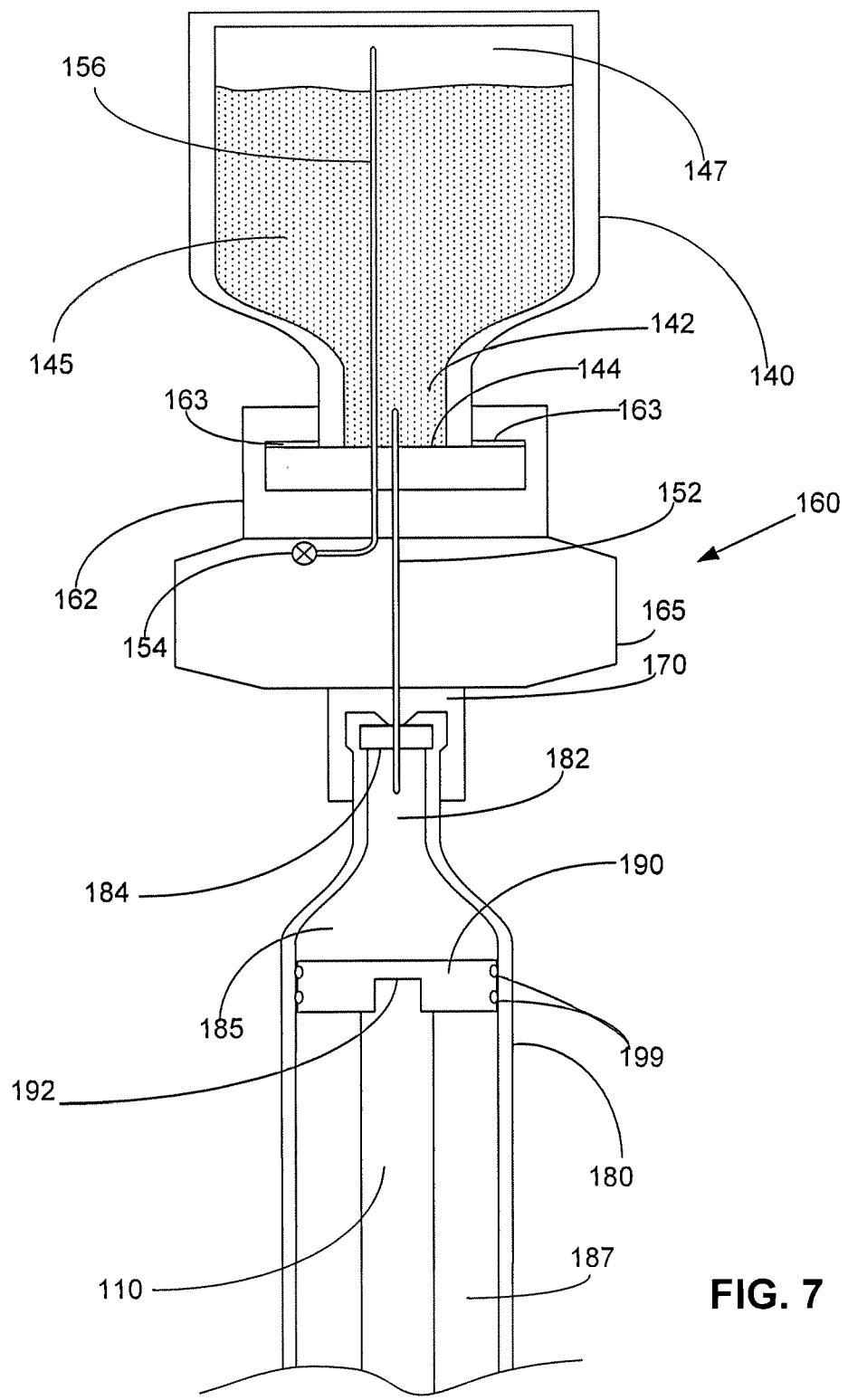
FIG. 7 is a cross-section of a portion of a medical device in accordance with an embodiment of the present invention.
Figure 8A:
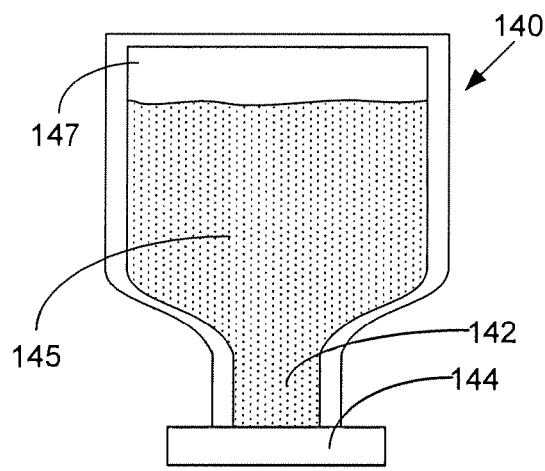
FIG. 8A is a cross-section of a portion of a medical device in accordance with an embodiment of the present invention.
Figure 8B:
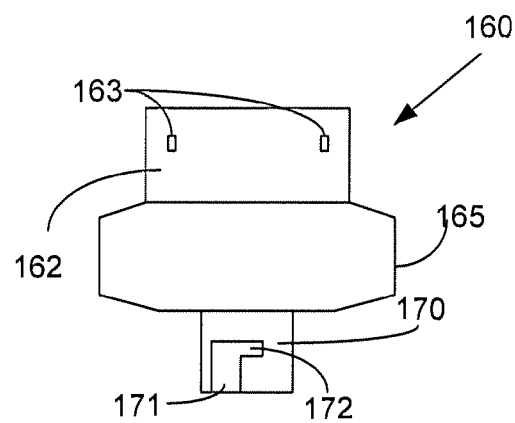
FIG. 8B is a cross-section of a portion of a medical device in accordance with an embodiment of the present invention.
Figure 8C:
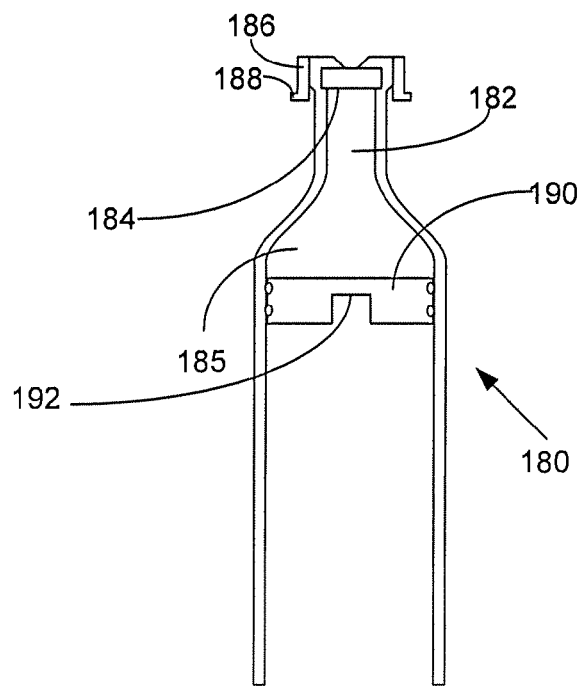
FIG. 8C is a cross-section of a portion of a medical device in accordance with an embodiment of the present invention.

FIGS. 7-8C illustrate a system 100 for transferring fluidic media in accordance with an embodiment of the present invention. The system 100 may include features similar to, employed as an embodiment of, and/or used with the medical device systems discussed throughout the disclosure (e.g., delivery device 12 in FIGS. 1-6C). Although the system 100 may include features similar or used with the embodiments of FIGS. 1-6C, it should be understood that the system 100 may also include some or all of the same features and operate in a manner similar to that shown and described in the embodiments of FIGS. 9-17. In addition, some or all of the features shown in FIGS. 1-6C and 9-17 may be combined in various ways and included in the embodiments shown in FIGS. 7-8C. Likewise, it should be understood that any of the features of the embodiments of FIGS. 7-8C may be combined or otherwise incorporated into any of the other embodiments of FIGS. 7-8C as well as any other embodiment herein discussed.

The system 100 may include, but is not limited to, a vial 140, a transfer guard 160, and a reservoir 180. The vial 140 may include a septum 144 located at a port 142 of the vial 140. The vial 140 may have an interior volume 145 for containing fluidic media. The reservoir 180 may have an interior volume 185 for containing fluidic media. The reservoir 180 may include a septum 184 located at a port 182 of the reservoir 180.

The plunger head 190 may be located within the reservoir 180 and may be moveable within the reservoir 180 to expand or contract the interior volume 185 of the reservoir 180. The plunger head 190 may be attached to or integrated with the plunger arm 110. The handle 130 may be operatively to the plunger arm 110.

The plunger head 190 may include at least one seal member 199, such as an o-ring, or the like, in contact with the reservoir 180. The interior volume 185 of the reservoir body 180 may be on one side of the seal member 199. The reservoir 180 may have a chamber 187 located on an opposite side of the seal member 199 from the interior volume 185 of the reservoir 180. The seal member 199 may be for facilitating movement within the reservoir 180 and/or to substantially prevent fluidic media from flowing from the interior volume 185 to the chamber 187 of the reservoir 180.

The transfer guard 160 may include a needle 152 for providing a fluid path from the interior volume 145 of the vial 140 to the interior volume 185 of the reservoir 180. The transfer guard 160 may be configured such that when the vial 140 is attached or otherwise mated to the transfer guard 160, the needle 152 pierces the septum 144 of the vial 140. The transfer guard 160 may be further configured such that when the reservoir 180 is attached or otherwise mated to the transfer guard 160, the needle 152 pierces the septum 184 of the reservoir 180. Thus, the transfer guard 160 may allow for establishing a fluid path from the vial 140 to the reservoir 180 through the needle 152.

In some embodiments, the transfer guard 160 may include a second needle 156. The second needle 156 may be able to pierce the septum 144 of the vial 140 when the vial 140 is connected to the transfer guard 160. An end of the second needle 156 may be located within a headspace 147 of the vial 140 above fluidic media within the interior volume 145 of the vial 140 in a case where the transfer guard 160 is connected to the vial 140. In other embodiments, the end of the second needle 156 may be in contact with fluidic media within the interior volume 145 of the vial 140 in a case where the transfer guard 160 is connected to the vial 140.

Another end of the second needle 156 may be connected to a check valve 154, such as a one-way valve, or the like. The check valve 154 may allow air to enter the interior volume 145 of the vial 140 through the second needle 156. In some embodiments, the check valve 154 may substantially prevent liquid from coming out of the vial 140 through the second needle 156 and/or the check valve 154. In various embodiments, the second needle 156 may allow for venting the headspace 147 or the interior volume 145 of the vial 140 to atmosphere to facilitate the transfer of fluidic media from the vial 140 to the reservoir 180.

The transfer guard 160 may have a body 165, a first end 162, and a second end 170. The first end 162 may be for supporting or otherwise receiving the vial 140 to attach or otherwise mate with the vial 140 to the transfer guard 160. For example, a portion of the vial 140 (e.g., portion corresponding to the port 142 of the vial 140) may be placed in the first end 162 of the transfer guard 160. As described above, the septum 144 of the vial 140 may be pierced by the needle 152 of the transfer guard 160 when the vial 140 is inserted into the first end 162 of the transfer guard 160.

In some embodiments, the first end 162 may be adapted to secure the vial 140 to the transfer guard 160 in any suitable manner known in the art, such as (but not limited to) friction fitting, snap-fitting, or the like. For example, the first end 162 of the transfer guard 160 may include at least one tab 163, annular rib, or the like for securing the vial 140 within the first end 162 of the transfer guard 160 once the vial 140 is inserted in the first end 162 of the transfer guard 160.

The second end 170 may be located opposite the first end 162. The second end 170 may be for supporting or otherwise receiving the reservoir 180 to attach or otherwise mate with the reservoir 180 to the transfer guard 160. For example, a portion of the reservoir 180 (e.g., portion corresponding to the port 182 of the reservoir 180) may be placed in the second end 170 of the transfer guard 160. The septum 184 of the reservoir 180 may be pierced by the needle 152 of the transfer guard 160 when the reservoir 180 is inserted into the second end 170 of the transfer guard 160.

In some embodiments, the second end 170 may be adapted to secure the reservoir 180 to the transfer guard 160 in any suitable manner known in the art, such as (but not limited to) friction fitting, snap-fitting, or the like. For example, as shown in FIGS. 7 and 8A-8C, the second end 170 of the transfer guard 160 may include one or more depressions or apertures 171 located within the second end 170 of the transfer guard 160. The port 182 portion of the reservoir 180 may include one or more tabs 186 for inserting into the one or more apertures 171 located in the second end 170 of the transfer guard 160. The port 182 portion of the reservoir 180 may further include at least one second tab 188 attached to each of the one or more tabs 186.

In some embodiments, the reservoir 180 and port 182 portion may be configured, for example, to be rotatable, at least partially, about the second end 170 of the transfer guard 160 to secure the reservoir 180 to the transfer guard 160. The second end 170 of the transfer guard 160 may further include one or more depressions 172 for receiving the at least one second tab 188 when the reservoir 180 and port 182 portion are rotated to secure the reservoir 180 to the transfer guard 160. As a result, the port 182 portion of the reservoir 180 may be inserted into the second end 170 of the transfer guard 160 so that the one or more tabs 186 fit into the apertures 171 and then rotated slightly until the at least one second tab 188 fits into place within the one or more depressions 172 to lock the reservoir 180 into the second end 170 of the transfer guard 160.

In some embodiments, the first end 162 and the vial 140 may be configured in the same manner as described above so that the one or more tabs 186 fit into the one or more apertures 171 and adapted to be rotatable slightly until the at least one second tab 188 fits into place within the one or more depressions 172. In some embodiments, the second end 170 of the transfer guard 160 may be configured to include at least one tab 163 for securing at least a portion of the reservoir 180 within the second end 170 of the transfer guard 160 similar to that described above with respect to the first end 162 of the transfer guard 160.

FIGS. 9-17 illustrates a system 200 for transferring fluidic media in accordance with an embodiment of the present invention. The system 200 may include features similar to, employed as an embodiment of, and/or used with the medical device systems discussed throughout the disclosure (e.g., delivery device 12 in FIGS. 1-6C). In addition, the system 200 may include features similar to the systems discussed throughout the disclosure or employed as an embodiments of the systems (e.g., system 100 in FIGS. 7-8C) discussed throughout the disclosure. In addition, some or all of the features shown in FIGS. 1-8C may be combined in various ways and included in the embodiments shown in FIG. 9-17. Likewise, it should be understood that any of the features of the embodiments of FIGS. 9-17 may be combined or otherwise incorporated into any of the other embodiments of FIGS. 9-17 as well as any other embodiment herein discussed.

In particular embodiments, the system 200 may be similar to the system 100 described with respect to FIGS. 7-8C. As shown, for example in FIGS. 9 and 10, the system 200 may include, but is not limited to, a vial 240, a transfer guard 260, a reservoir 280, a plunger head 290, a plunger arm 210, a plunger arm casing 230, and a handle 220.

FIGS. 11-14B illustrate a reservoir 280, which may include features similar to or employed as an embodiment of the reservoir 180 (e.g., FIGS. 7 and 8C), that may be employed in the system 200 according to various embodiments of the present invention. As previously described, the reservoir 280 may have an interior volume 285 for containing fluidic media. The reservoir 280 may include a septum 284 located at a port 282 of the reservoir 280. In various embodiments, the reservoir 280 may be made of various suitable materials, including, but not limited to, glass, plastic, TOPAS® polymer (or any other cyclic olefin copolymer (or polymer)), or the like. The reservoir 280 may be of any suitable shape and/or size and may be adapted to hold any volume of fluidic media depending on needs of user-patients.

The port 282 may be for expelling fluidic media contained in the interior volume 285 of the reservoir 280, for example, when the reservoir 280 is used with a delivery device (not shown) for delivering fluidic media to a user-patient. In various embodiments, the port 282 of the reservoir 280 may be for allowing fluidic media to flow into the interior volume 285 of the reservoir 280 (i.e., to fill the interior volume 285 of the reservoir 280), for example, from the vial 240 via the needle 252 of the transfer guard 260. Thus, in some embodiments, the port 282 may allow for filling the reservoir 280, for example, when connected to the transfer guard 260 connected to the vial 240, and for expelling fluidic media, for example, when connected to a delivery device.

In some embodiments, the port 282 may be near an edge of the reservoir 280 to facilitate a purging of bubbles in the interior volume 285 of the reservoir 280. For example, the user-patient could tilt the reservoir 280 (or the entire system 200) slightly to allow bubbles to escape through the port 282.

In some embodiments, an end 289 of the reservoir 280 may be open to allow the plunger head 290 and/or at least a portion of the plunger arm 210 to be insertable into the reservoir 280. For example, in a case where the port 282 is located on a first end of the reservoir 280, a second end opposite the first end may be the end 289 of the reservoir 280.

The plunger head 290 or a portion thereof may be made of Bromobutyl rubber, silicone rubber, or any other suitable material and/or any derivative thereof. The plunger head 290 may be locatable within the reservoir 280 and may be moveable in an axial direction of the reservoir 280 to expand or contract the interior volume 285 of the reservoir 280. The plunger head 290 may be advanced within the reservoir 280 to expel fluidic media contained in the interior volume 285 of the reservoir 280 out the port 282 of the reservoir 280, for example, when the reservoir 280 is used with the delivery device for delivering fluidic media to the user-patient. In various embodiments, the plunger head 290 may be adapted to be moveable within the reservoir 280 to draw fluidic media into the reservoir 280 from the vial 240, for example, in a case where the reservoir 280 is connected to the transfer guard 260 and the vial 240 is connected to the transfer guard 260.

The plunger head 290 may have a front portion 297 and a rear portion 298. The front portion 297 of the plunger head 290 may be in contact with fluidic media contained in the interior volume 285 of the reservoir 280. In some embodiments, the front portion 297 of the plunger head 290 may comprise a material compatible with fluidic media contained or to be contained in the interior volume 285 of the reservoir 280.

The rear portion 298 of the plunger head 290 may be connected or connectable to an end of the plunger arm 210 in any suitable manner. For example, the rear portion 298 of the plunger head 290 may include at least one aperture 291 or the like for receiving at least one tab 211 or the like of the plunger arm 210. The at least one tab 211 may be snap-fit into the at least one aperture 291 to connect the plunger arm 210 to the rear portion 298 of the plunger head 290. In some embodiments, the plunger head 290 may contain at least one tab 292 or the like and the plunger arm 210 may include at least one aperture 212 or the like for receiving the at least one tab 292. In various other embodiments, the plunger arm 210 may be connected to the plunger head 290 and/or the rear portion 298 of the plunger head 290 in any suitable manner, such as, but not limited to, an adhesive, friction fitting, laser welding, magnetic coupling, or the like.

The plunger arm 210 may be moveable in an axial direction within the plunger arm casing 230 and the reservoir 280. In some embodiments, the plunger arm 210 and the rear portion 298 of the plunger head 290 may be integral to one another. In such embodiments, the plunger arm 210 and the integrated rear portion 298 may be integral with the plunger head 290 or be connectable to the plunger head 290. In other embodiments, the plunger arm 210 and the rear portion 298 of the plunger head 290 may be separate components adapted to be connected together as previously described.

The plunger arm 210 may include an engagement side 218 for operatively engaging a drive member (not shown), drive linkage, or the like when connected to the delivery device. For example, the engagement side 218 of the plunger arm 210 and the drive member may be complementing gears, complementing threaded or toothed members, or the like, that may operatively engage each other. The drive member may be a drive screw, drive rack, or the like.

The drive member may be operatively connected to a motor to move or otherwise actuate the drive member to actuate or otherwise cause the plunger arm 210 to move within the plunger arm casing 230 and/or the reservoir 280. Accordingly, the plunger arm 210 may move within the reservoir 280 to expand or contact the interior volume 285 of the reservoir 280 to fill the reservoir 280 with fluidic media or expel fluidic media from the reservoir 280. In some embodiments, the drive motor may be operatively engaged or directly engaged with the engagement side 218 of the plunger arm 210 to actuate or otherwise cause the plunger arm 210 to move within the plunger arm casing 230 and/or the reservoir 280.

Figure 16A:
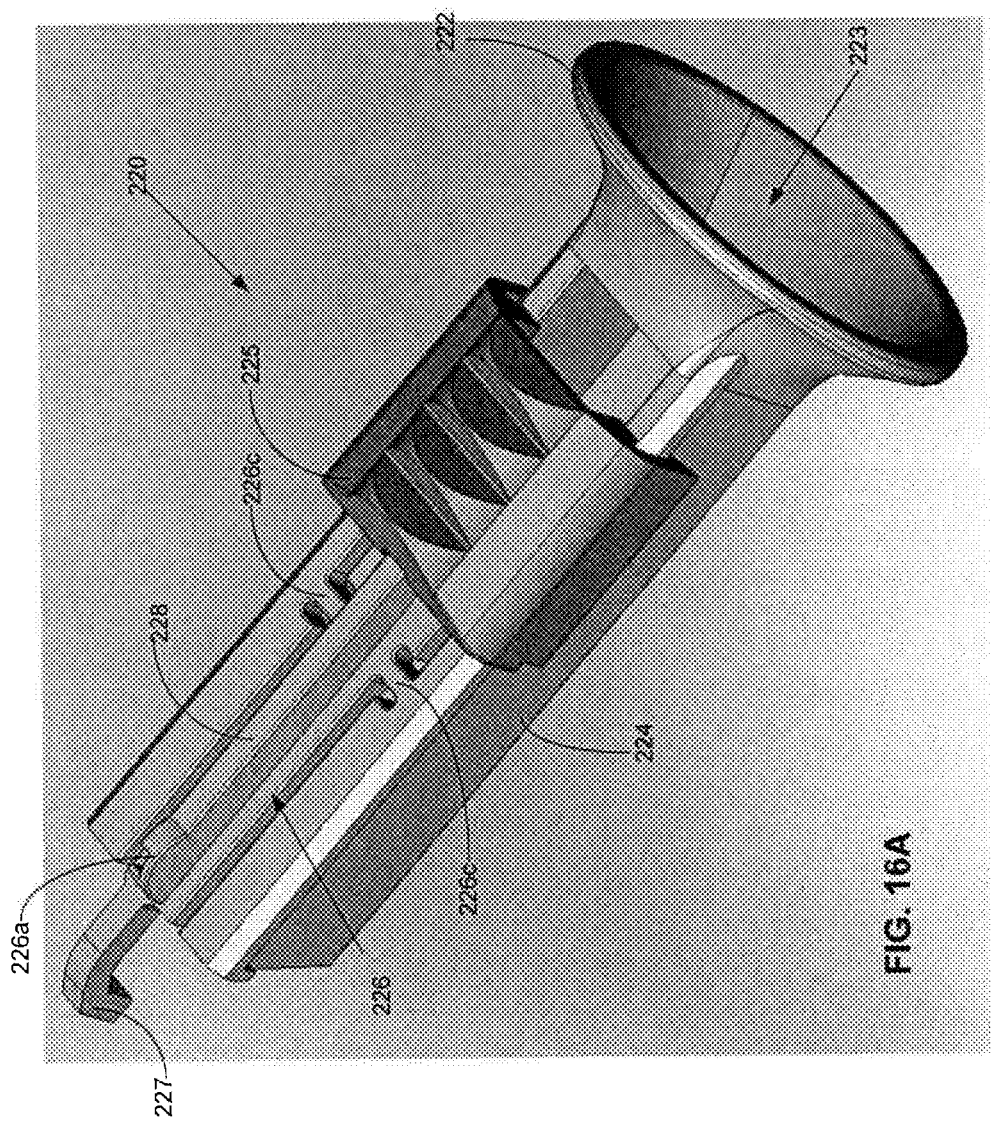
FIG. 16A illustrates a portion of a medical device in accordance with an embodiment of the present invention.

The plunger arm casing 230 may be for supporting the plunger arm 210 as the plunger arm 210 is moved along the plunger arm casing 230 and/or the reservoir 280, for example, from actuation by the drive member or the handle 220 (e.g., FIGS. 16A-17). At least one side of the plunger arm 210 may be in contact with one or more interior sides of the plunger arm casing 230. In some embodiments, the plunger arm casing 230 may be for aligning or otherwise guiding the plunger arm 210, for example, into the reservoir 280 as the plunger arm 210 moves along the reservoir 280, for example, from actuation by the drive member or the handle 270 (discussed later). The casing 230 may be made of a material of suitable strength and durability such as, but not limited to, plastic, metal, glass (e.g., tempered glass), composite material, and/or the like. In some embodiments, the casing 230 may be made of the same material as the reservoir 280.

In various embodiments, the plunger arm casing 230 may be sized and configured to substantially or completely envelop the plunger arm 210, for example, when the plunger head 290 is drawn substantially near the end 289 of the reservoir 280 (e.g., in a case where the reservoir 280 has been filled or substantially filled with fluidic media). Thus in some embodiments, the plunger arm 210 or a portion thereof may be located within the reservoir 280 and/or the plunger arm casing 230 during use of the system 200 for transferring fluidic media from the vial 240 to the reservoir 280 or during operation of the delivery device.

In some embodiments, the plunger arm casing 230 may have an opening 236 for allowing a portion of the engagement side 218 of the plunger arm 210 to operatively engage the drive member or drive motor. In such embodiments, the plunger arm 210 may be surrounded by the plunger arm casing 230 and/or the reservoir 280 except for the portion of the engagement side 218 of the plunger arm 210 exposed by the opening 236, which may be free from (i.e., not surrounded by) the plunger arm casing 230 and/or the reservoir 280. This may allow the drive member to operatively engage the engagement side 218 of the plunger arm 210 while the plunger arm 210 or a portion thereof remains in the plunger arm casing 230 and/or the reservoir 280.

The system 200 may include a reservoir cover 234 that may be sized and configured to cover the end 289 of the reservoir 280. The reservoir cover 234 may cover the end 289 of the reservoir 280 or be configured to fit within or to the end 289 of the reservoir 280 to seal or close the end 289 of the reservoir 280. The reservoir cover 234 may be integral with or separate from the plunger arm casing 230. The reservoir cover 234 may have an opening 233 (refer to FIG. 17) to allow the plunger arm 210 to move into or out of the reservoir 280. The reservoir cover 234 may be made of a material of suitable strength and durability such as, but not limited to, plastic, metal, glass (e.g., tempered glass), composite material, and/or the like. In some embodiments, the reservoir cover 234 may be made of the same material as the plunger arm casing 230 and/or the reservoir 280.

In some embodiments, the reservoir cover 234 and/or the plunger arm casing 230 may be configured for minimizing an expansion of the reservoir 280 in one or more dimensions. In such embodiments, by fitting the reservoir cover 234 to the end 289 of the reservoir 280, the reservoir cover 234 may help retain a shape of the reservoir 280, for example, as the interior volume 285 of the reservoir body 280 fills with fluidic media.

In some embodiments, the reservoir system 200 may include at least one support flange 217 positioned on the plunger arm 210 and the rear portion 298 of the plunger head 290. The support flange 217 may provide additional structural strength to the plunger arm 210 and/or the plunger head 290. For example, the support flange 217 may have a triangular configuration and be positioned with one side of the support flange 217 connected to a surface of the plunger arm 210 and a second side of the support flange 217 connected to the rear portion 298 of the plunger head 290.

In addition to or alternative to, a second support flange (not shown) may be positioned with one side of the second support flange connected to a different surface of the plunger arm 210 and a second side of the second support flange connected to the rear portion 298 of the plunger head 290. In various embodiments, support flanges may located along any suitable location for providing support to the plunger arm 210 and/or the plunger head 290 or any other component. One or both of the support flanges may be made of a material of suitable strength and durability such as, but not limited to, plastic, metal, glass (e.g., tempered glass), composite material, and/or the like. In some embodiments, the one or both of the support flanges may be made of the same material as the plunger arm casing 230, the reservoir cover 234, and/or the reservoir 280.

In some embodiments, the plunger arm casing 230 may include a groove 238 or the like for allowing a portion of the handle 220 (e.g., FIGS. 16A-17) to operatively engage the plunger arm 210. Thus, the handle 220 may be operatively engaged to the plunger arm 210 through the groove 238 to transfer force to actuate or otherwise move the plunger arm 210 along the plunger arm casing 230 and/or the reservoir 280.

With reference to FIGS. 9, 10, 12, 13, and 17, in various embodiments, the second end 270 may be connected to or integrated with the transfer guard 260. The second end 270 may comprise a body 273. The body 273 may have a hollow interior 275 for removably receiving at least a portion of the reservoir 280. In further embodiments, the body 273 may be adapted such that the reservoir 280 may be placed entirely in the hollow interior 275 of the body 273. In embodiments where the port 282 is located near an edge of the reservoir 280, the second end 270 may be off center from the transfer guard 260. The body 273 may be made of a material of suitable strength and durability such as, but not limited to, plastic, metal, glass (e.g., tempered glass), composite material, and/or the like. In some embodiments, the body 273 may be made of the same material as the transfer guard 260 or a portion thereof.

In some embodiments, the body 273 may include one or more fill lines 278 or other indicators for providing information located, for example, on a front side 273a of the body 273. In other embodiments, the one or more fill lines 278 may be arranged in any suitable manner or along any suitable portion of the body 273. For instance, the one or more fill lines 278 may correspond to amount(s) of fluidic media contained in the reservoir 280. Thus, for example, the user-patient can fill the reservoir 280 accurately with a specific amount (e.g., 0.5 ml, 1 ml, etc.) of fluidic media from the vial 240 by comparing an amount of fluidic media in the interior volume 285 of the reservoir 280 with the one or more fill lines 278.

In some embodiments, an indicator 279 may be provided corresponding to a location of the port 282 of the reservoir 280 in a case where the reservoir is mated with the second end 270. In such embodiments, the user-patient can direct bubbles in the interior volume 285 of the reservoir 280 toward the indicator, for example by titling the reservoir 280 or the system 200, to purge the bubbles.

In further embodiments, the body 273 may be adapted to allow a user-patient to view at least some contents in the reservoir 280. For example, portions of the body 273 may have an opening to expose at least a portion of the reservoir 280 within the hollow interior 275 of the body 273. In such embodiments, the user-patient may be able to hold the reservoir though the opening to further support the reservoir 280 during use of the system 200. As another example, the body 273 or portions thereof may be at least partially transparent to visually expose at least a portion of the reservoir 280 within the hollow interior 275 of the body 273.

In some embodiments, the body 273 may be configured to secure the reservoir 280 or a portion thereof in the hollow interior 275 once the reservoir 280 is placed in the hollow interior 275. For example, the body 273 may have one or more tabs 277 or the like within the hollow interior 275 for securing or otherwise preventing accidental removal of the reservoir 280 from the hollow interior 275.

In some embodiments, the body 273 may be adapted to be flexible. This may allow, for example, the user-patient to squeeze at least a portion of the body 273, such as, but not limited to, along one or more sides 273*b* of the body 270 to release the one or more tabs 277 to allow the reservoir 280 to be inserted into or removed from the hollow interior 275.

Figure 14C:
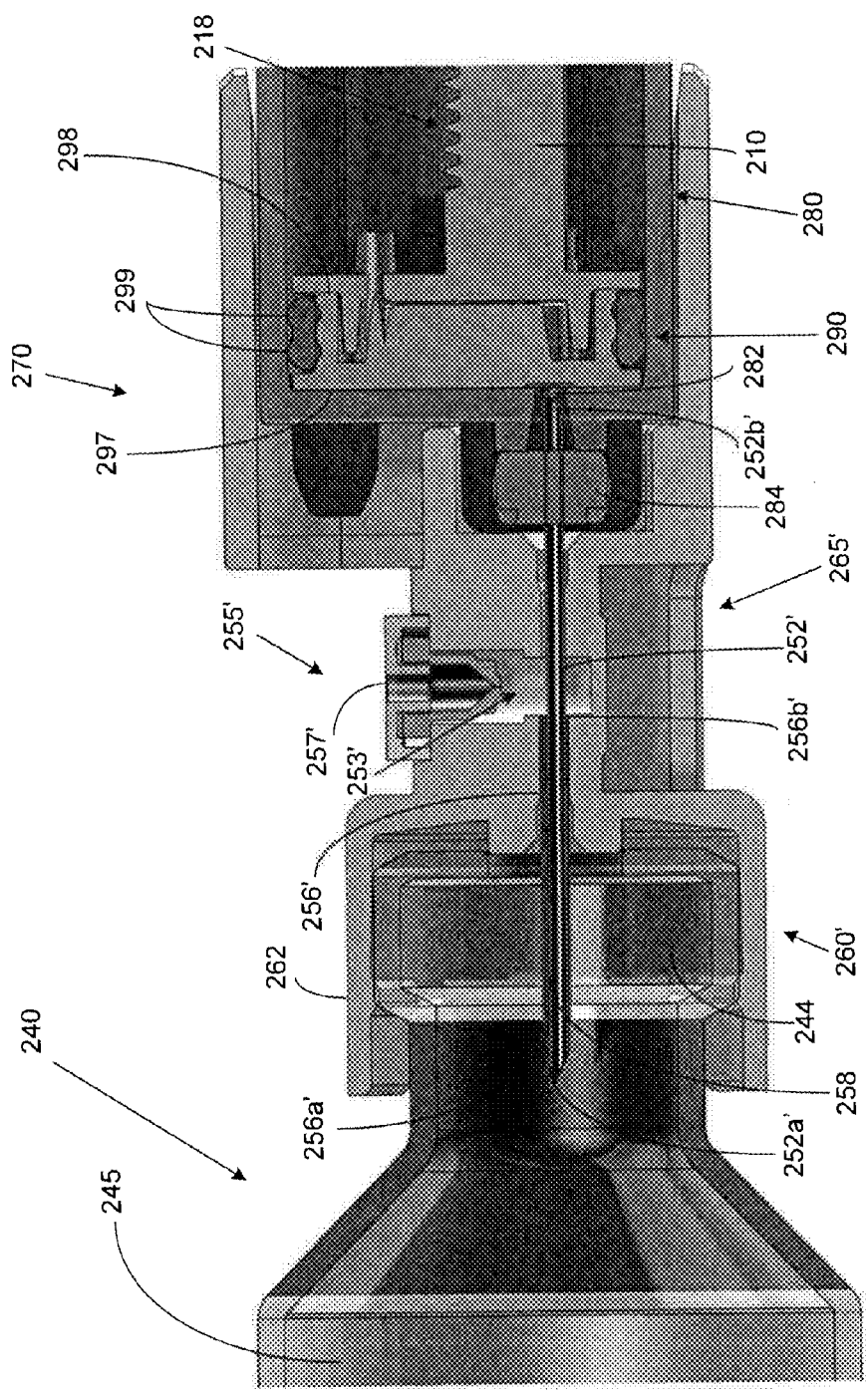
FIG. 14C is a cross-section of a portion of a medical device in accordance with an embodiment of the present invention.

With reference to FIGS. 13-14B, in various embodiments, the transfer guard 260 may include a body 265. The first needle 252 may be arranged to pass through the body 265 to provide a fluid flow path between the vial 240 and the reservoir 280. In some embodiments, the body 265 may be formed by connecting the first end 262 and the second end 270 together (e.g., FIG. 13). In other embodiments, the body 265, the first end 262, and the second end 270 may be integral with each other (e.g., FIG. 14C).

In some embodiments, the transfer guard 260 may include an inner body 250 located within the body 265. In such embodiments, the first needle 252 may be arranged to pass through the body 265 and the inner body 250. The inner body 250 may be made of a material of suitable strength and durability such as, but not limited to, plastic, metal, glass (e.g., tempered glass), composite material, and/or the like. In some embodiments, the inner body 250 may be made of the same material as the body 273 and/or the transfer guard 260 or a portion thereof. The inner body 250 may be separate from or integrated with the body 265 of the transfer guard 260.

The first needle 252 may have a first end 252*a* (and/or opening along the first needle 252) and a second end 252*b* (and/or opening along the first needle 252) opposite each other. The first end 252*a* may be for arrangement in the vial 240, for example, in contact with fluidic media in the interior volume 245 or the headspace 247 of the vial 240 in a case where the vial 240 is connected to the transfer guard 260. The second end 252*b* may be for arrangement in the reservoir 280, for example, through the septum 284 into the port 282 of the reservoir 280. In some embodiments, one or more of the ends 252*a*, 252*b* of the first needle 252 may be beveled to provide one or more sharp ends to the first needle 252. In other embodiments, one or more of the ends 252*a*, 252*b* of the first needle 252 may be flat.

The second needle 256 may have a first end 256*a* (and/or opening along the second needle 256) and a second end 256*b* (and/or opening along the second needle 256) opposite each other. The first end 256*a* may be for arrangement in the vial 240, for example, in contact with fluidic media in the interior volume 245 or a headspace (e.g., 147 in FIG. 7) of the vial 240 in a case where the vial 240 is connected to the transfer guard 260. The second end 256*b* may be arranged in the transfer guard 260 or external to the transfer guard 260. In some embodiments, one or more of the ends 256*a*, 256*b* of the second needle 256 may be flat. In other embodiments, one or more of the ends 256*a*, 256*b* of the second needle 256 may be beveled to provide one or more sharp ends to the second needle 256.

In some embodiments, the inner body 250 may have a chamber 253. In further embodiments, the transfer guard 260 may include a mechanism to allow air to flow in one direction, such as, a valve 255 or a membrane, arranged within the chamber 253. The valve 255 may be, but is not limited to, an umbrella valve, duckbill valve, ball check valve, or the like.

The second end 256*b* of the second needle 256 may be in communication with the chamber 253. The valve 255 may regulate flow of air into and/or out of the interior volume 245 of the vial 240 through the second needle 256. Thus, the valve 255 may allow for equalizing pressure within the interior volume 245 of the vial 240, for example, relative to atmosphere to facilitate transfer of fluidic media from the vial 240 to the reservoir 280. In yet further embodiments, the valve 255 may be provided with a seal member 259 to prevent fluidic media from flowing past the seal member 259 and/or to facilitate movement of the valve 255 in the chamber 253. In some embodiments, one or more retaining members, such as ridge 251, or the like, may be for retaining the valve 255 within the chamber 253.

In some embodiments, the valve 255 may have a channel 257 to allow the chamber 253 to communicate with atmosphere, for example, to allow air to flow into or out of the chamber 253. In some embodiments, the valve 255 may substantially prevent liquid from coming out of the vial 240 through the second needle 256 and/or the valve 255. In various embodiments, the second needle 256 may allow for venting the headspace or the interior volume 245 of the vial 240 to atmosphere to facilitate the transfer of fluidic media from the vial 240 to the reservoir 280. Thus, in such embodiments, the valve 255 may allow pressure within the vial to be equalized or otherwise regulated to facilitate the transfer of fluidic media from the vial 240 to the reservoir 280.

In some embodiments, such as the embodiment exemplified in FIG. 14C, the system 200 may employ a transfer guard 260', which may include features similar to the transfer guard 260 (e.g., 9-14B). The transfer guard 260' may include a body 265'. A first needle 252' may be arranged to pass through the body 265' to provide a fluid flow path between the vial 240 and the reservoir 280. In some embodiments, the body 265' may be formed by connecting the first end 262 and the second end 270 together (e.g., FIG. 13). In other embodiments, the body 265', the first end 262, and the second end 270 may be integral with each other (e.g., FIG. 14C).

The first needle 252' may have a first end 252*a*' (and/or opening along the first needle 252') and a second end 252*b*' (and/or opening along the first needle 252') opposite each other. The first end 252*a*' may be for arrangement in the vial 240, for example, in contact with fluidic media in the interior volume 245 or the headspace 247 of the vial 240 in a case where the vial 240 is connected to the transfer guard 260'. The second end 252*b*' may be for arrangement in the reservoir 280, for example, through the septum 284 into the port 282 of the reservoir 280. In some embodiments, one or more of the ends 252a', 252b' of the first needle 252' may be beveled to provide one or more sharp ends to the first needle 252'. In other embodiments, one or more of the ends 252a', 252b' of the first needle 252' may be flat.

At least a portion of the first needle 252' may be arranged within at least a portion of a second needle 256'. In some embodiments, the first needle 252' (or at least a portion thereof) may be concentrically arranged within the second needle 256' (or at least a portion thereof). Thus in various embodiments, the first needle 252' and the second needle 256' may share a common axis. In other embodiments, the first needle 252' (or at least a portion thereof) may be concentrically arranged within the second needle 256' (or at least a portion thereof) such that the first needle 252' is offset from the second needle 256' with a spacing 258. Thus in various embodiments, the first needle 252' and the second needle 256' each have their own axis parallel to each other.

In some embodiments, the transfer guard 260' may have a chamber 253'. The chamber 253' may be in communication with the interior volume 245 of the vial 240, for example, through the second needle 256'. For instance, one end 256a' (and/or opening) of the second needle 256' may be in communication with the interior volume 245 of the vial 240, and another end 256b' (and/or opening), opposite the end 256a', may be in communication with the chamber 253'. In some embodiments, one or more of the ends 256a', 256b' of the second needle 256' may be flat. In other embodiments, one or more of the ends 256a', 256b' of the second needle 256' may be beveled to provide one or more sharp ends to the second needle 256'.

In further embodiments, the transfer guard 260' may include a mechanism to allow air to flow in one direction, such as, a valve 255' or a membrane, arranged within the chamber 253'. The valve 255' may be, but is not limited to, an umbrella valve, duckbill valve, ball check valve, or the like.

The valve 255' may regulate flow of air into and/or out of the interior volume 245 of the vial 240 through the needle 254'. Thus, the valve 255' may allow for equalizing pressure within the interior volume 245 of the vial 240, for example, relative to atmosphere to facilitate transfer of fluidic media from the vial 240 to the reservoir 280. In yet further embodiments, the valve 255' may be provided with a seal member (e.g., 259 in FIG. 14B) to prevent fluidic media from flowing past the seal member and/or to facilitate movement of the valve 255' in the chamber 253'. In some embodiments, one or more retaining members, such as ridge (e.g., 251 in FIG. 14B), or the like, may be for retaining the valve 255' within the chamber 253'.

In some embodiments, the valve 255' may have a channel 257' to allow the chamber 253' to communicate with atmosphere, for example, to allow air to flow into or out of the chamber 253'. In some embodiments, the valve 255' may substantially prevent liquid from coming out of the vial 240. In various embodiments, the second needle 256' may allow for venting a headspace (e.g., 147 in FIG. 7) or the interior volume 245 of the vial 240 to atmosphere to facilitate the transfer of fluidic media from the vial 240 to the reservoir 280. Thus, in such embodiments, the valve 255' may allow pressure within the vial to be equalized or otherwise regulated to facilitate the transfer of fluidic media from the vial 240 to the reservoir 280.

Accordingly, in various embodiments, a second needle for equalizing pressure within a vial or to otherwise regulate or facilitate the transfer of fluidic media from the vial to a reservoir may be concentrically arranged around a first needle for transferring the fluidic media from the vial to the reservoir.

Figure 9:
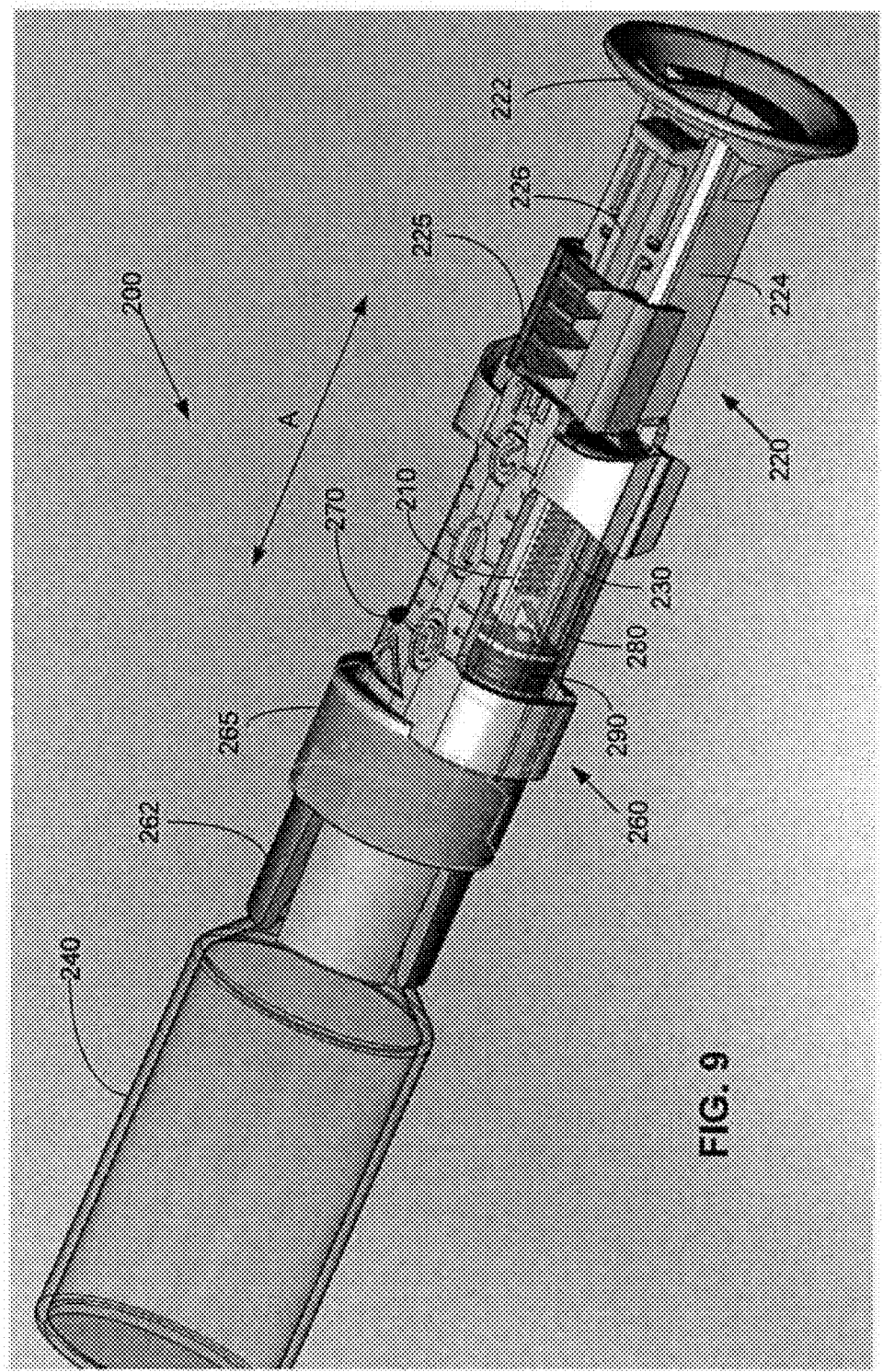
FIG. 9 illustrates a medical device in accordance with an embodiment of the present invention.
Figure 10:
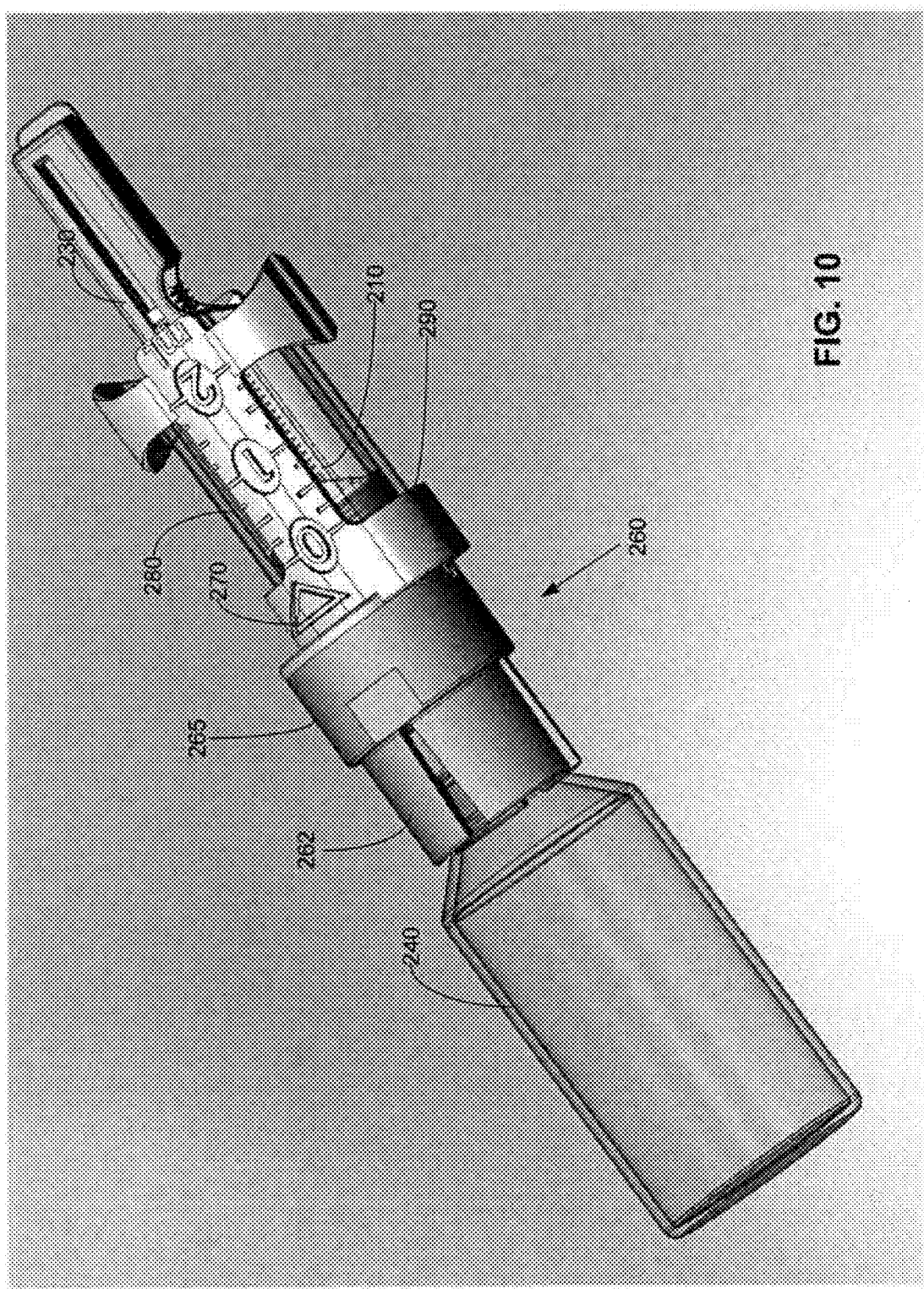
FIG. 10 illustrates a portion of a medical device in accordance with an embodiment of the present invention.
Figure 11:
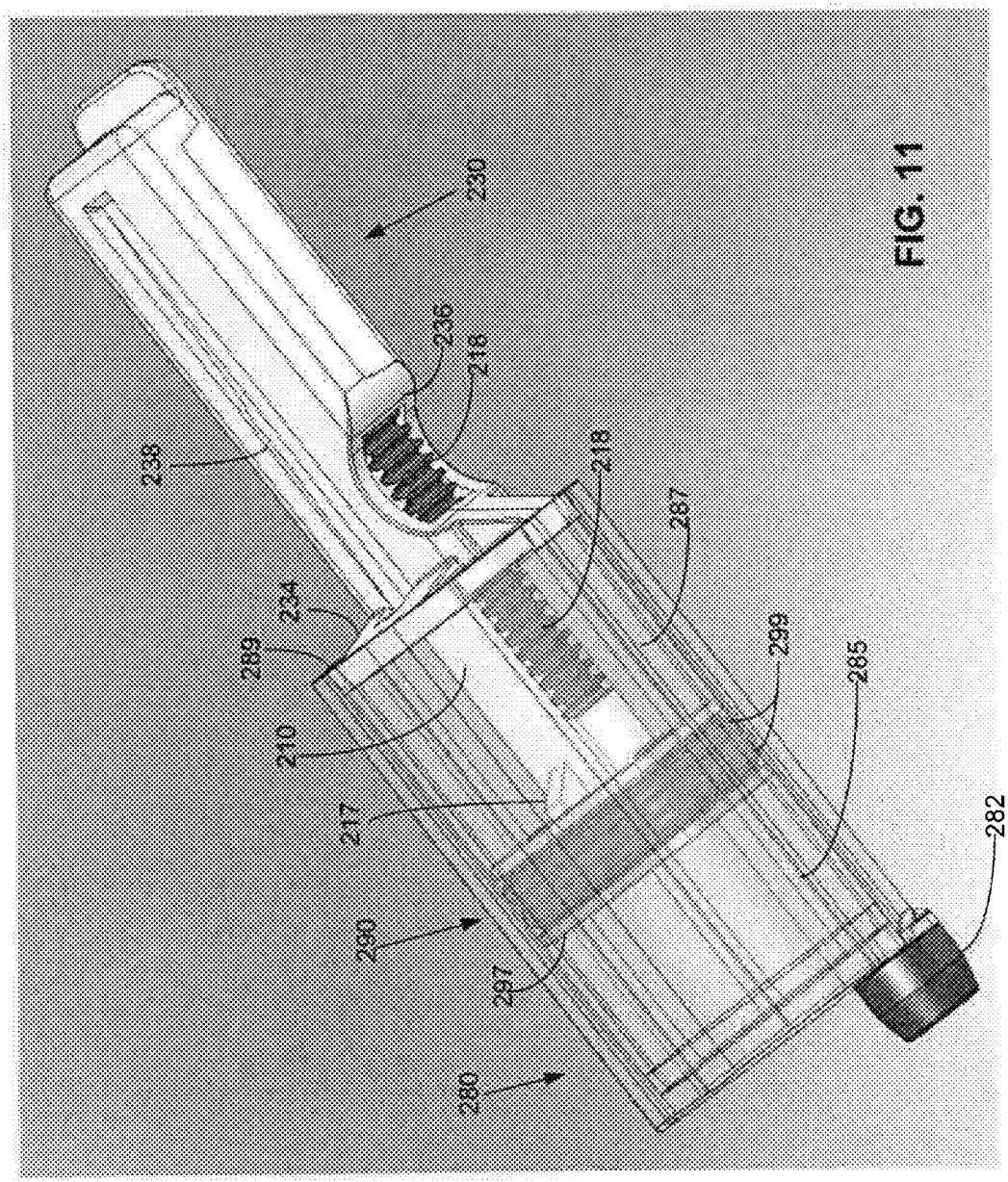
FIG. 11 illustrates a portion of a medical device in accordance with an embodiment of the present invention.
Figure 12:
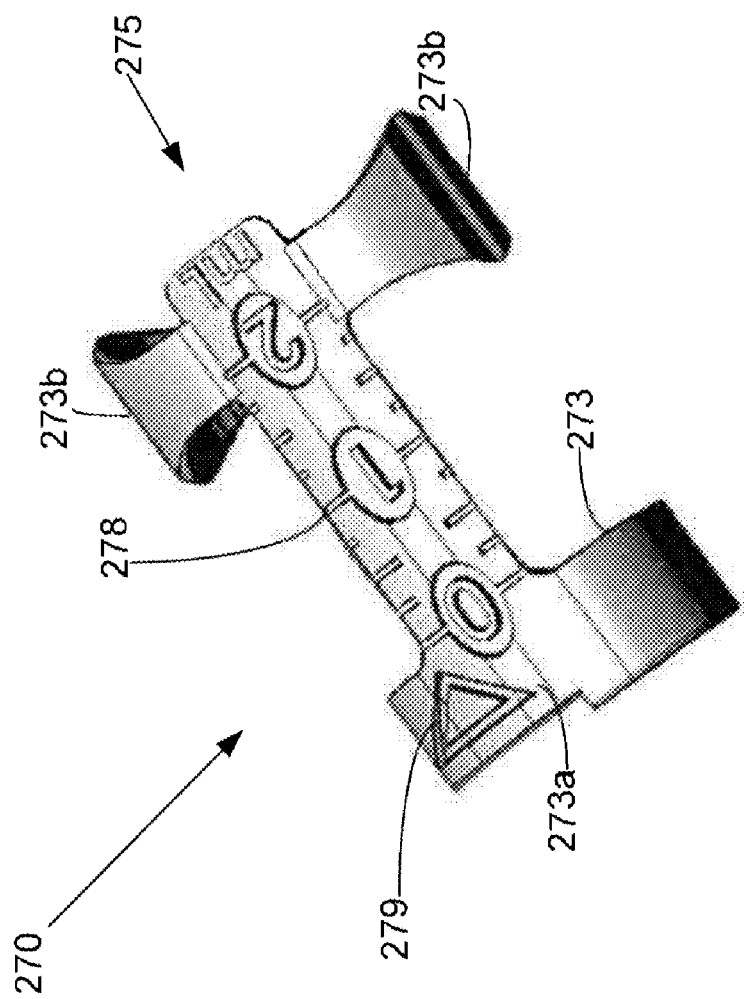
FIG. 12 illustrates a portion of a medical device in accordance with an embodiment of the present invention.
Figure 15:
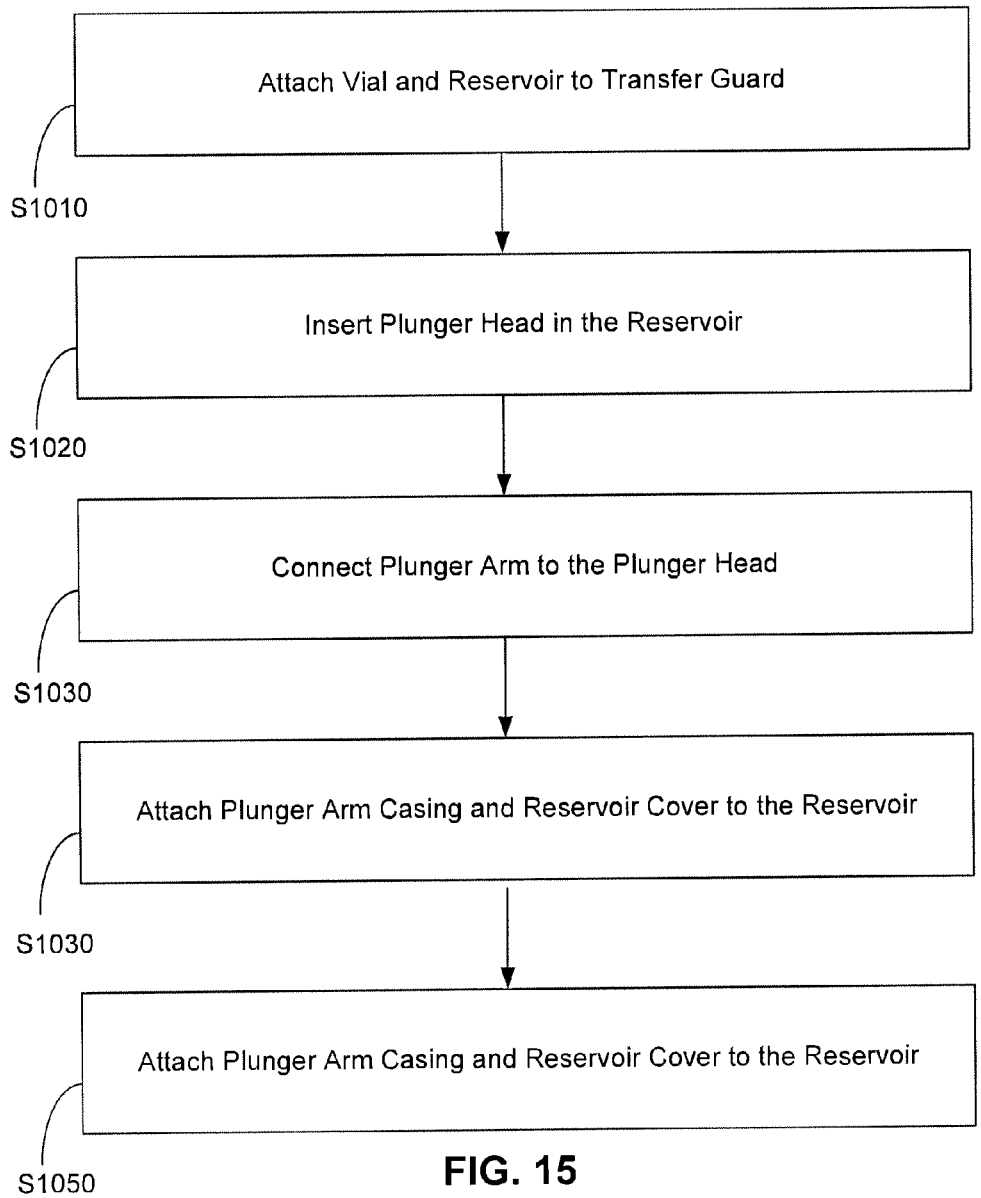
FIG. 15 illustrates a flowchart for using a medical device in accordance with an embodiment of the present invention.

Referring to FIGS. 10 and 15 to operate the system 200, in step S1010, the vial 240 and the reservoir 280 may be attached or otherwise mated with the first end 262 and the second end 270 of the transfer guard 260 respectively. Then in step S1020, the plunger head 290 may be inserted into the reservoir 280. Next in step S1030, the plunger arm 210 may be connected to the plunger head 290 (if not integrated or already connected). In step S1040, the plunger arm casing 230 and reservoir cover 234 may be arranged to support the plunger arm 210 and cover the reservoir 280. Then in step S1050, the handle 220 may be operatively connected to the plunger arm 210 as shown in FIG. 9.

With reference to FIGS. 9, 10, and 16A-17, the handle 220 may be for operatively connecting to or otherwise engaging the plunger arm 210 to actuate or otherwise cause movement of the plunger arm 210 by advancing or withdrawing the handle 220 along line A. Because the plunger head 290 may be attached to the plunger arm 210, movement of the handle 220 may advance or draw the plunger head 290 within the reservoir 280. Accordingly, fluidic media may be drawn from the vial 240 into the reservoir 280 by drawing the handle 290 and the operatively engaged plunger arm 210 and plunger head 290, for example, away from the reservoir 280.

The handle 220 may have a body 224 that may be sized and configured to cover at least a portion of the plunger arm casing 230. The body 224 may have an interior cavity 223 for receiving at least a portion of the plunger arm casing 230 within the interior cavity 223 through an opening 223a. The body 224 may be for supporting the plunger arm casing 230, for example, as the plunger arm 210 is moved along the plunger arm casing 230 and/or the reservoir 280. The body 224 may be made of a material of suitable strength and durability such as, but not limited to, plastic, metal, glass (e.g., tempered glass), composite material, and/or the like. In some embodiments, the body 224 may be made of the same material as the plunger arm casing 230.

At least one side of the plunger arm casing 230 may be in contact with one or more interior sides of the body 224. In some embodiments, the body 224 may be for aligning the plunger arm casing 230 when the plunger arm casing 230 is placed within the interior cavity 223 of the body 224. In various embodiments, the plunger arm casing 230 may remain substantially still as the handle 220 actuates the plunger arm 210 along the plunger arm casing 230 and/or the reservoir 280.

The handle 220 may be configured to operatively engage and disengage the plunger arm 210 and/or the plunger arm casing 230 in any suitable manner. In some embodiments, the handle 220 may have an engagement portion 226 for operatively engaging and disengaging the plunger arm 210. Accordingly, movement of the handle 220 may actuate the plunger arm 210 and therefore the plunger head 290 attached to the plunger arm 210 to allow fluidic media to be drawn from the vial 240 to the reservoir 280 via the first needle 252. The engagement portion 226 may have a first end 226a and a second end 226b.

In some embodiments, a movable member, such as a slide 225, may be mounted on the engagement portion 226 and may be moveable at least between the first end 226a and the second end 226b to lock and unlock the handle 220 to the plunger arm 210. The first end 226a and the second end 226b may be for preventing the slide 225 from being dismantled accidentally from the engagement portion 226. In some embodiments, the engagement portion 226 may include a rail 228 or the like for allowing the slide 225 to slide or otherwise move at least between the first end 226a and the second end 226b.

In other embodiments, the moveable member may be a rotatable member (not shown). The rotatable member may be moveable (e.g., rotatable) at least between the first end 226a and the second end 226b to lock and unlock the handle 220 to the plunger arm 210. For example, the rotatable member may be rotatable about an axis of the handle 220. In other embodiments, the moveable member may be a hinged member (not shown) for locking and unlocking the handle 220 to the plunger arm 210.

In some embodiments, the engagement portion 226 may be pivotally mounted, cantilevered, biased, or otherwise positioned relative to the body 224 of the handle 220. In such embodiments, the engagement portion 226 may be adapted for pivotal movement about a pivot point 226c. The engagement portion 226 may include a member, such as a finger 227 or the like, for engaging an aperture 211 or the like in the plunger arm 210. Accordingly, the finger 227 may be pivotable or otherwise moveable toward and away from the body 224 as the engagement portion 226 is pivoted about the pivot point 226c to engage and disengage the plunger arm 210.

In further embodiments, the engagement portion 226 may be pivoted about the pivot point 226c by movement of the slide 225. For example, by moving the slide 225 toward the second end 226b (e.g., FIG. 16A), a front portion of the engagement portion 226, which may include the finger 227, may pivot upward. Accordingly, the plunger arm casing 230 having the plunger arm 210 within may be placed at least partially in the interior cavity 223 of the body 224. Then by moving the slide 225 toward the first end 226a (e.g., FIG. 9), the front portion of the engagement portion 226 and the finger 227 may pivot downward to allow the finger 227 to engage the aperture 211 in the plunger arm 210, for example, through the groove 238 in the plunge arm casing 230. The finger 227 may remain engaged in the aperture 211 while the slide 225 remains at or near the first end 226a.

Once engaged, the handle 220 may be drawn away from the reservoir 240 to draw fluidic media from the vial 240 through the first needle 252 of the transfer guard 260 to the reservoir 280. After the reservoir 280 is sufficiently filled with a desired amount of fluidic media, the slide 225 may be moved toward the second end 226b to allow the front portion of the engagement portion 226 and the finger 227 to pivot upward to disengage the plunger arm 210. Accordingly, the user-patient may remove the reservoir 280, the plunger arm 210, and/or the plunger arm casing 230 and insert the appropriate components in the delivery device (not shown) or provide another reservoir, plunger arm, and/or plunger arm casing in the system 200.

The handle 220 may include a base 222. The base 222 may be for standing the system 200 vertically on a support surface. In some embodiments, the base 222 may include an adhesive or the like for securing the handle 220 to the support surface. Thus in some embodiments, in a case where the base 222 of the system 200 on a support surface and fluidic media is to be drawn from the vial 240 to the reservoir 280, the reservoir 280 (along with the transfer guard 260 and the vial 240) may be drawn away from the handle 220, which may remain substantially still, to transfer fluidic media. In some embodiments, the base 222 may be for providing the user-patient with a gripping area to use the system 200, for example, to pull the handle 220 to draw fluidic media into the reservoir 200.

Referring to FIGS. 9, 13, and 15, various embodiments of the system 200 may allow for simplifying a filling process of the reservoir 280 with fluidic media from the vial 240. After step S1050, the handle 220 operatively engaged with the plunger arm 210 may be pulled or otherwise moved away from the reservoir 280. As the handle 220 moves away from the reservoir 280, the attached plunger arm 210 and plunger head 290 may be moved within the reservoir 280 to increase the interior volume 285 of the reservoir 280. The movement of the plunger head 290 may draw fluidic media from the vial 240 through the first needle 252 of the transfer guard 260 to the interior volume 285 of the reservoir 280 to transfer fluidic media to the reservoir 280.

With reference to FIGS. 9-17, in various embodiments, the steps of the process 1000 may be performed in any suitable order. For example, the vial 240 may be attached to the transfer guard 260 after the handle 220 is operatively engaged with the plunger arm 210. As another example, the plunger arm 210 may be connected to the plunger head 290 before the plunger head 290 is placed in the reservoir 280. In some embodiments, the plunger head 290 may be advanced within the reservoir 280 toward the port 282 of the reservoir 280 before starting the filling process of the reservoir 280, for example, to prime the system 200.

The system 200 may be used to fill the interior volume 285 of the reservoir 280, or a portion thereof. In some embodiments, the system 200 may be configured such that the interior volume 285 of the reservoir 280 is completely filled or sufficiently filled when the handle 290 is drawn as far from the reservoir 280 as the system allows.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for transferring fluidic media, the system comprising:
   a transfer guard for providing a fluid path from a vial to a reservoir;
   a handle configured to be operatively engagable to a plunger arm connected to a plunger head arranged for movement in an axial direction of the reservoir, the handle comprising an engagement portion configured for pivotal movement to operatively engage and disengage the plunger arm, the engagement portion having an extension and the plunger arm having an aperture for receiving the extension when the engagement portion of the handle operatively engages the plunger arm; and
   a casing configured to allow the plunger arm to move in the axial direction relative to the reservoir to move the plunger head in the axial direction within the reservoir, the handle configured to cover at least a portion of the casing;
   the transfer guard and the handle configured such that fluidic media is transferred from the vial to the reservoir in a case where the handle is operatively engaged to the plunger arm and the handle is moved in the axial direction relative to the reservoir.

2. The system of claim 1, the casing having an opening for allowing the handle to operatively engage the plunger arm.

3. The system of claim 1, the handle comprising a slide adapted to cause the pivotal movement of the engagement portion to operatively engage and disengage the plunger arm.

4. The system of claim 3,
   the slide adapted to move at least between a first position and a second position;

the engagement portion configured to engage the plunger arm when the slide is moved to the first position; and the engagement portion configured to disengage the plunger arm when the slide is moved to the second position.

5. The system of claim 1, the extension of the engagement portion for extending through an opening in the casing to operatively engage the aperture in the plunger arm and for allowing the extension of the engagement portion to move along the opening as the plunger arm is moved by the handle.

6. The system of claim 1, the transfer guard having an end for mating with the reservoir, the end comprising a body configured to envelop the reservoir.

7. The system of claim 6, the body adapted to allow fluidic media in the reservoir to be viewable through the body in a case where the reservoir is connected to the end of the transfer guard and the reservoir contains fluidic media.

8. The system of claim 7, the body having an opening for allowing fluidic media in the reservoir to be viewable and for allowing a user-patient to provide further support to the reservoir during use of the system.

9. The system of claim 6, the body having one or more fill lines for measuring a volume of fluidic media in the reservoir.

10. A system for transferring fluidic media, the system comprising:
a transfer guard for providing a fluid path from a vial to a reservoir;
a handle configured to be operatively engagable to a plunger arm connected to a plunger head arranged for movement in an axial direction of the reservoir; and
a casing configured to allow the plunger arm to move in the axial direction relative to the reservoir to move the plunger head in the axial direction within the reservoir, the handle configured to cover at least a portion of the casing;
the transfer guard and the handle configured such that fluidic media is transferred from the vial to the reservoir in a case where the handle is operatively engaged to the plunger arm and the handle is moved in the axial direction relative to the reservoir;
the transfer guard having a chamber, the transfer guard comprising:
a first needle for connecting the interior volume of the vial to the interior volume of the reservoir to provide a fluid flow path from the interior volume of the vial to the interior volume of the reservoir;
a second needle for connecting the chamber and the interior volume of the vial; and
an air flow control mechanism arranged within the chamber and configured to allow air to flow in one direction in a case where the second needle connects the chamber and the vial and the plunger head is moved within the reservoir to transfer fluidic media from the interior volume of the vial to the interior volume of the reservoir.

11. The system of claim 10, the air flow control mechanism configured to allow the chamber to communicate with atmosphere to equalize pressure relative to atmosphere in the interior volume of the vial in a case where the second needle connects the chamber and the vial and the plunger head is moved within the reservoir to transfer fluidic media from the interior volume of the vial to the interior volume of the reservoir.

12. The system of claim 10, wherein the air flow control mechanism comprises a membrane configured to allow air to flow in one direction.

13. The system of claim 10, wherein the air flow control mechanism comprises a valve.

14. The system of claim 13, wherein the valve comprises at least one of an umbrella valve and a duckbill valve configured to allow air to flow in one direction.

15. A method of making a system for transferring fluidic media, the method comprising:
providing a transfer guard for providing a fluid path from a vial to a reservoir;
configuring a handle to be operatively engagable to a plunger arm connected to a plunger head arranged for movement in an axial direction of the reservoir, including providing the handle with an engagement portion configured for pivotal movement to operatively engage and disengage the plunger arm, the engagement portion having an extension and the plunger arm having an aperture for receiving the extension when the engagement portion of the handle operatively engages the plunger arm;
configuring a casing to allow the plunger arm to move in the axial direction relative to the reservoir to move the plunger head in the axial direction within the reservoir;
configuring the handle to cover at least a portion of the casing; and
configuring the transfer guard and the handle such that fluidic media is transferred from the vial to the reservoir in a case where the handle is operatively engaged to the plunger arm and the handle is moved in the axial direction relative to the reservoir.

* * * * *